United States Patent
Cabiri et al.

(10) Patent No.: US 11,759,573 B2
(45) Date of Patent: Sep. 19, 2023

(54) BENT FLUID PATH ADD ON TO A PREFILLED RESERVOIR

(71) Applicant: West Pharma. Services, IL, Ltd., Ra'anana (IL)

(72) Inventors: Oz Cabiri, Hod Hasharon (IL); Paul H. Norton, St. Augustine, FL (US); Ran Hezkiahu, Herzliya (IL); Richard Brough, Scottsdale, AZ (US)

(73) Assignee: West Pharma. Services, IL, Ltd., Ra'anana (IL)

( * ) Notice: Subject to any disclaimer, the term of this patent is extended or adjusted under 35 U.S.C. 154(b) by 63 days.

(21) Appl. No.: 17/395,670

(22) Filed: Aug. 6, 2021

(65) Prior Publication Data
US 2021/0361871 A1 Nov. 25, 2021

Related U.S. Application Data

(60) Division of application No. 15/766,719, filed as application No. PCT/US2016/056213 on Oct. 10, (Continued)

(51) Int. Cl.
*A61M 5/28* (2006.01)
*A61M 5/31* (2006.01)
(Continued)

(52) U.S. Cl.
CPC ............ *A61M 5/28* (2013.01); *A61M 5/3134* (2013.01); *A61M 5/3202* (2013.01);
(Continued)

(58) Field of Classification Search
CPC .... A61M 5/28; A61M 5/3134; A61M 5/3202; A61M 5/3204; A61M 5/34;
(Continued)

(56) References Cited

U.S. PATENT DOCUMENTS

| 232,432 A | 9/1880 | Allison |
| 1,125,887 A | 1/1915 | Schimmel |

(Continued)

FOREIGN PATENT DOCUMENTS

| CN | 1505535 A | 6/2004 |
| CN | 1747683 A | 3/2006 |

(Continued)

OTHER PUBLICATIONS

US 8,333,733 B2, 12/2012, Lanigan et al. (withdrawn)
(Continued)

*Primary Examiner* — Tasnim Mehjabin Ahmed
(74) *Attorney, Agent, or Firm* — Blank Rome LLP

(57) ABSTRACT

An add-on for a self-injector including an adaptor and a bent fluid path is provided. The adaptor includes at least one coupling sized and shaped to couple the adaptor to a fluid reservoir. The bent fluid path is configured at a first end to penetrate tissue and coupled at a second end to the adaptor. The add-on coupled to the fluid reservoir forms an integral self-injector cartridge unit configured to be sterilized and filled with an injectable. The adaptor is configured to couple to a self-injector at least one of a plurality of reservoirs having different sizes and tip types.

17 Claims, 7 Drawing Sheets

Related U.S. Application Data 2016, now Pat. No. 11,116,908, which is a continuation of application No. 15/204,542, filed on Jul. 7, 2016, now Pat. No. 10,576,207.

(60) Provisional application No. 62/281,536, filed on Jan. 21, 2016, provisional application No. 62/284,806, filed on Oct. 9, 2015.

(51) Int. Cl.
| | |
|---|---|
| A61M 5/34 | (2006.01) |
| A61M 5/32 | (2006.01) |
| B65D 1/36 | (2006.01) |
| B65D 25/10 | (2006.01) |
| B65D 5/50 | (2006.01) |
| B65D 21/02 | (2006.01) |
| A61M 5/142 | (2006.01) |
| A61M 5/158 | (2006.01) |
| A61M 5/145 | (2006.01) |

(52) U.S. Cl.
CPC ............ *A61M 5/3204* (2013.01); *A61M 5/34* (2013.01); *B65D 1/36* (2013.01); *B65D 5/503* (2013.01); *B65D 21/0233* (2013.01); *B65D 25/108* (2013.01); *A61M 5/1456* (2013.01); *A61M 5/14248* (2013.01); *A61M 2005/1581* (2013.01); *A61M 2005/312* (2013.01); *A61M 2005/341* (2013.01); *A61M 2205/3306* (2013.01); *A61M 2207/00* (2013.01)

(58) Field of Classification Search
CPC ............ A61M 5/14248; A61M 5/1456; A61M 2005/1581; A61M 2005/312; A61M 2005/341; A61M 2205/3306; A61M 2207/00
See application file for complete search history.

(56) References Cited

U.S. PATENT DOCUMENTS

| | | |
|---|---|---|
| 1,321,550 A | 11/1919 | Frank et al. |
| 1,704,921 A | 3/1929 | Nicoll |
| 1,795,530 A | 3/1931 | Cowan et al. |
| 1,795,630 A | 3/1931 | Wilson |
| 2,453,590 A | 11/1948 | Poux |
| 2,589,426 A | 3/1952 | Ogle |
| 2,677,373 A | 5/1954 | George |
| 2,702,547 A | 2/1955 | Glass |
| 2,860,635 A | 11/1958 | Wilburn |
| 3,203,269 A | 8/1965 | Perrine |
| 3,212,685 A | 10/1965 | James et al. |
| 3,585,439 A | 6/1971 | Schneeberger |
| 3,623,474 A | 11/1971 | Heilman et al. |
| 3,705,582 A | 12/1972 | Stumpf et al. |
| 3,708,945 A | 1/1973 | Klettke |
| 3,794,028 A | 2/1974 | Mueller et al. |
| 3,834,387 A | 9/1974 | Brown |
| 3,994,295 A | 11/1976 | Wulff |
| 4,085,747 A | 4/1978 | Lee |
| 4,189,065 A | 2/1980 | Herold |
| 4,195,636 A | 4/1980 | Behnke |
| 4,218,724 A | 8/1980 | Kaufman |
| 4,254,768 A | 3/1981 | Ty |
| 4,273,122 A | 6/1981 | Whitney et al. |
| 4,300,554 A | 11/1981 | Hessberg et al. |
| 4,324,262 A | 4/1982 | Hall |
| 4,403,987 A | 9/1983 | Gottinger |
| 4,425,120 A | 1/1984 | Sampson et al. |
| 4,435,173 A | 3/1984 | Siposs et al. |
| 4,465,478 A | 8/1984 | Sabelman et al. |
| 4,502,488 A | 3/1985 | Degironimo et al. |
| 4,504,263 A | 3/1985 | Steuer et al. |
| 4,549,554 A | 10/1985 | Markham |
| 4,564,054 A | 1/1986 | Gustavsson |
| 4,565,543 A | 1/1986 | Bekkering et al. |
| 4,583,974 A | 4/1986 | Kokernak |
| 4,585,439 A | 4/1986 | Michel |
| 4,599,082 A | 7/1986 | Grimard |
| 4,601,702 A | 7/1986 | Hudson |
| 4,636,201 A | 1/1987 | Ambrose et al. |
| 4,664,654 A | 5/1987 | Strauss |
| 4,685,903 A | 8/1987 | Cable et al. |
| 4,695,274 A | 9/1987 | Fox |
| 4,698,055 A | 10/1987 | Sealfon |
| 4,702,738 A | 10/1987 | Spencer |
| 4,704,105 A | 11/1987 | Adorjan et al. |
| 4,710,178 A | 12/1987 | Henri et al. |
| 4,729,208 A | 3/1988 | Galy et al. |
| 4,735,311 A | 4/1988 | Lowe et al. |
| 4,737,144 A | 4/1988 | Choksi |
| 4,772,272 A | 9/1988 | Mcfarland |
| 4,810,215 A | 3/1989 | Kaneko |
| 4,810,249 A | 3/1989 | Haber et al. |
| 4,813,426 A | 3/1989 | Haber et al. |
| 4,840,185 A | 6/1989 | Hernandez |
| 4,850,966 A | 7/1989 | Grau et al. |
| 4,861,341 A | 8/1989 | Woodburn |
| 4,863,434 A | 9/1989 | Bayless |
| 4,867,743 A | 9/1989 | Vaillancourt |
| 4,874,383 A | 10/1989 | Mcnaughton |
| 4,882,575 A | 11/1989 | Kawahara |
| 4,886,499 A | 12/1989 | Cirelli et al. |
| 4,892,521 A | 1/1990 | Laico et al. |
| 4,897,083 A | 1/1990 | Martell |
| 4,900,310 A | 2/1990 | Ogle, II |
| 4,915,702 A | 4/1990 | Haber |
| 4,919,569 A | 4/1990 | Wittenzellner |
| 4,919,596 A | 4/1990 | Slate et al. |
| 4,923,446 A | 5/1990 | Page et al. |
| 4,929,241 A | 5/1990 | Kulli |
| 4,950,241 A | 8/1990 | Ranford |
| 4,950,246 A | 8/1990 | Muller |
| 4,957,490 A | 9/1990 | Byrne et al. |
| 4,964,866 A | 10/1990 | Szwarc |
| 4,994,045 A | 2/1991 | Ranford |
| 4,998,924 A | 3/1991 | Ranford |
| 5,019,051 A | 5/1991 | Hake |
| 5,051,109 A | 9/1991 | Simon |
| 5,062,828 A | 11/1991 | Waltz |
| D322,671 S | 12/1991 | Szwarc |
| 5,088,988 A | 2/1992 | Talonn et al. |
| 5,109,850 A | 5/1992 | Blanco et al. |
| 5,112,317 A | 5/1992 | Michel |
| 5,114,406 A | 5/1992 | Gabriel et al. |
| 5,127,910 A | 7/1992 | Talonn et al. |
| 5,131,816 A | 7/1992 | Brown et al. |
| 5,147,326 A | 9/1992 | Talonn et al. |
| 5,156,599 A | 10/1992 | Ranford et al. |
| 5,190,521 A | 3/1993 | Hubbard et al. |
| 5,217,437 A | 6/1993 | Talonn et al. |
| 5,246,670 A | 9/1993 | Haber et al. |
| 5,254,096 A | 10/1993 | Rondelet et al. |
| 5,267,977 A | 12/1993 | Feeney, Jr. |
| 5,269,762 A | 12/1993 | Armbruster et al. |
| 5,275,582 A | 1/1994 | Wimmer |
| 5,282,593 A | 2/1994 | Fast |
| 5,295,966 A | 3/1994 | Stern et al. |
| 5,298,023 A | 3/1994 | Haber et al. |
| 5,300,045 A | 4/1994 | Plassche, Jr. |
| 5,318,522 A | 6/1994 | D'Antonio |
| 5,338,311 A | 8/1994 | Mahurkar |
| 5,342,313 A | 8/1994 | Campbell et al. |
| 5,348,544 A | 9/1994 | Sweeney et al. |
| 5,366,498 A | 11/1994 | Brannan et al. |
| 5,376,785 A | 12/1994 | Chin et al. |
| 5,383,865 A | 1/1995 | Michel |
| D356,150 S | 3/1995 | Duggan et al. |
| 5,415,645 A | 5/1995 | Friend et al. |
| 5,456,360 A | 10/1995 | Griffin |
| 5,478,315 A | 12/1995 | Brothers et al. |
| 5,478,316 A | 12/1995 | Bitdinger et al. |

(56) References Cited

U.S. PATENT DOCUMENTS

| | | | |
|---|---|---|---|
| 5,482,446 | A | 1/1996 | Williamson et al. |
| 5,496,274 | A | 3/1996 | Graves et al. |
| 5,501,665 | A | 3/1996 | Jhuboo et al. |
| 5,505,709 | A | 4/1996 | Funderburk et al. |
| 5,562,624 | A | 10/1996 | Righi et al. |
| 5,562,686 | A | 10/1996 | Sauer et al. |
| 5,593,390 | A | 1/1997 | Castellano et al. |
| 5,609,580 | A | 3/1997 | Kwiatkowski et al. |
| 5,611,785 | A | 3/1997 | Mito et al. |
| 5,616,132 | A | 4/1997 | Newman |
| 5,624,400 | A | 4/1997 | Firth et al. |
| 5,637,095 | A | 6/1997 | Nason et al. |
| 5,643,218 | A | 7/1997 | Lynn et al. |
| 5,645,530 | A | 7/1997 | Boukhny et al. |
| 5,645,955 | A | 7/1997 | Maglica |
| 5,647,853 | A | 7/1997 | Feldmann et al. |
| 5,658,256 | A | 8/1997 | Shields |
| 5,662,678 | A | 9/1997 | Macklin |
| 5,672,160 | A | 9/1997 | Oesterlind et al. |
| 5,690,618 | A | 11/1997 | Smith et al. |
| 5,697,908 | A | 12/1997 | Imbert et al. |
| 5,697,916 | A | 12/1997 | Schraga |
| 5,725,500 | A | 3/1998 | Micheler |
| 5,728,075 | A | 3/1998 | Levander |
| D393,314 | S | 4/1998 | Meisner et al. |
| 5,741,275 | A | 4/1998 | Wyssmann |
| 5,766,186 | A | 6/1998 | Faraz et al. |
| 5,776,103 | A | 7/1998 | Kriesel et al. |
| 5,795,675 | A | 8/1998 | Maglica |
| 5,800,420 | A | 9/1998 | Gross et al. |
| 5,807,375 | A | 9/1998 | Gross et al. |
| 5,810,167 | A | 9/1998 | Fujii |
| 5,810,784 | A | 9/1998 | Tamaro |
| 5,814,020 | A | 9/1998 | Gross |
| 5,830,187 | A | 11/1998 | Kriesel et al. |
| 5,836,920 | A | 11/1998 | Robertson |
| 5,848,991 | A | 12/1998 | Gross et al. |
| 5,851,197 | A | 12/1998 | Marano et al. |
| 5,858,001 | A * | 1/1999 | Tsals .................. A61M 5/1454 604/232 |
| 5,858,008 | A | 1/1999 | Capaccio |
| 5,868,710 | A | 2/1999 | Battiato et al. |
| 5,893,842 | A | 4/1999 | Imbert |
| 5,894,015 | A | 4/1999 | Rechtin |
| 5,919,167 | A | 7/1999 | Mulhauser et al. |
| 5,926,596 | A | 7/1999 | Edwards et al. |
| 5,931,814 | A | 8/1999 | Alex et al. |
| 5,941,850 | A | 8/1999 | Shah et al. |
| 5,944,699 | A | 8/1999 | Barrelle et al. |
| 5,948,392 | A | 9/1999 | Haslwanter et al. |
| 5,954,697 | A | 9/1999 | Srisathapat et al. |
| 5,957,895 | A | 9/1999 | Sage et al. |
| 5,968,011 | A | 10/1999 | Larsen et al. |
| 5,989,221 | A | 11/1999 | Hjertman |
| 5,993,423 | A | 11/1999 | Choi |
| 6,004,296 | A | 12/1999 | Jansen et al. |
| 6,004,297 | A | 12/1999 | Steenfeldt-Jensen et al. |
| 6,033,245 | A | 3/2000 | Yamkovoy |
| 6,033,377 | A | 3/2000 | Rasmussen et al. |
| 6,045,533 | A | 4/2000 | Kriesel et al. |
| 6,064,797 | A | 5/2000 | Crittendon et al. |
| 6,074,369 | A | 6/2000 | Sage et al. |
| 6,079,979 | A * | 6/2000 | Riitano .................. A61C 5/40 433/81 |
| 6,162,197 | A | 12/2000 | Mohammad |
| 6,186,979 | B1 | 2/2001 | Dysarz |
| 6,186,982 | B1 | 2/2001 | Gross et al. |
| 6,189,292 | B1 | 2/2001 | Odell et al. |
| 6,200,289 | B1 | 3/2001 | Hochman et al. |
| 6,200,296 | B1 | 3/2001 | Dibiasi et al. |
| 6,224,569 | B1 | 5/2001 | Brimhall |
| 6,248,093 | B1 | 6/2001 | Moberg |
| 6,270,481 | B1 | 8/2001 | Mason et al. |
| 6,277,095 | B1 | 8/2001 | Kriesel et al. |
| 6,277,098 | B1 | 8/2001 | Klitmose et al. |
| 6,277,099 | B1 | 8/2001 | Strowe et al. |
| 6,287,283 | B1 | 9/2001 | Ljunggreen et al. |
| 6,293,925 | B1 | 9/2001 | Safabash et al. |
| 6,302,633 | B1 | 10/2001 | Poe |
| 6,336,729 | B1 | 1/2002 | Pavelle et al. |
| 6,345,968 | B1 | 2/2002 | Shupe |
| 6,362,591 | B1 | 3/2002 | Moberg |
| 6,377,848 | B1 | 4/2002 | Garde et al. |
| 6,391,005 | B1 | 5/2002 | Lum et al. |
| 6,423,029 | B1 | 7/2002 | Elsberry |
| D461,243 | S | 8/2002 | Niedospial |
| D465,026 | S | 10/2002 | May et al. |
| 6,458,102 | B1 | 10/2002 | Mann et al. |
| 6,485,461 | B1 | 11/2002 | Mason et al. |
| 6,485,465 | B2 | 11/2002 | Moberg et al. |
| 6,500,150 | B1 * | 12/2002 | Gross .................. A61M 5/50 604/110 |
| 6,503,231 | B1 | 1/2003 | Prausnitz et al. |
| 6,511,336 | B1 | 1/2003 | Turek et al. |
| 6,517,517 | B1 | 2/2003 | Farrugia et al. |
| D471,274 | S | 3/2003 | Diaz et al. |
| D471,983 | S | 3/2003 | Hippolyte et al. |
| 6,554,800 | B1 | 4/2003 | Nezhadian et al. |
| 6,555,986 | B2 | 4/2003 | Moberg |
| 6,558,351 | B1 | 5/2003 | Steil et al. |
| 6,565,541 | B2 | 5/2003 | Sharp |
| 6,585,695 | B1 | 7/2003 | Adair et al. |
| 6,589,229 | B1 | 7/2003 | Connelly et al. |
| 6,595,956 | B1 | 7/2003 | Gross et al. |
| 6,595,960 | B2 | 7/2003 | West et al. |
| 6,645,181 | B1 | 11/2003 | Lavi et al. |
| 6,652,482 | B2 | 11/2003 | Hochman |
| 6,656,158 | B2 | 12/2003 | Mahoney et al. |
| 6,656,159 | B2 | 12/2003 | Flaherty |
| 6,659,980 | B2 | 12/2003 | Moberg et al. |
| 6,673,033 | B1 | 1/2004 | Sciulli et al. |
| 6,679,862 | B2 | 1/2004 | Diaz et al. |
| 6,685,678 | B2 | 2/2004 | Evans et al. |
| 6,689,118 | B2 | 2/2004 | Alchas et al. |
| 6,699,218 | B2 | 3/2004 | Flaherty et al. |
| 6,719,141 | B2 | 4/2004 | Heinz et al. |
| 6,722,916 | B2 | 4/2004 | Buccinna et al. |
| 6,743,211 | B1 | 6/2004 | Prausnitz et al. |
| 6,749,587 | B2 | 6/2004 | Flaherty |
| 6,752,783 | B2 | 6/2004 | Hung et al. |
| 6,752,787 | B1 | 6/2004 | Causey et al. |
| 6,767,336 | B1 | 7/2004 | Kaplan |
| 6,768,425 | B2 | 7/2004 | Flaherty et al. |
| 6,786,890 | B2 | 9/2004 | Preuthun et al. |
| 6,800,071 | B1 | 10/2004 | Mcconnell et al. |
| 6,805,687 | B2 | 10/2004 | Dextradeur et al. |
| 6,817,990 | B2 | 11/2004 | Yap et al. |
| 6,824,529 | B2 | 11/2004 | Gross et al. |
| 6,843,782 | B2 | 1/2005 | Gross et al. |
| 6,854,620 | B2 | 2/2005 | Ramey |
| 6,905,298 | B1 | 6/2005 | Haring |
| 6,907,679 | B2 | 6/2005 | Yarborough et al. |
| 6,908,452 | B2 | 6/2005 | Diaz et al. |
| 6,960,192 | B1 | 11/2005 | Flaherty et al. |
| 6,979,316 | B1 | 12/2005 | Rubin et al. |
| 6,997,727 | B1 | 2/2006 | Legrady et al. |
| 7,001,360 | B2 | 2/2006 | Veasey et al. |
| 7,004,104 | B2 | 2/2006 | Kundus |
| 7,004,929 | B2 | 2/2006 | McWethy et al. |
| 7,025,226 | B2 | 4/2006 | Ramey |
| 7,033,338 | B2 | 4/2006 | Vilks et al. |
| 7,034,223 | B2 | 4/2006 | Fan et al. |
| 7,048,715 | B2 | 5/2006 | Diaz et al. |
| 7,060,054 | B2 | 6/2006 | Nissels |
| 7,060,059 | B2 | 6/2006 | Keith et al. |
| 7,063,684 | B2 | 6/2006 | Moberg |
| 7,066,909 | B1 | 6/2006 | Peter et al. |
| 7,094,221 | B2 | 8/2006 | Veasey et al. |
| 7,097,637 | B2 | 8/2006 | Triplett et al. |
| 7,112,187 | B2 | 9/2006 | Karlsson |
| 7,128,727 | B2 | 10/2006 | Flaherty et al. |
| 7,144,384 | B2 | 12/2006 | Gorman et al. |
| 7,193,521 | B2 | 3/2007 | Moberg et al. |
| D544,092 | S | 6/2007 | Lewis |

(56) References Cited

U.S. PATENT DOCUMENTS

| | | |
|---|---|---|
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |
| RE39,923 E | 11/2007 | Blom |
| 7,291,132 B2 | 11/2007 | Deruntz et al. |
| 7,291,159 B2 | 11/2007 | Schmelzeisen-Redeker et al. |
| 7,303,549 B2 | 12/2007 | Flaherty et al. |
| 7,306,578 B2 | 12/2007 | Gray et al. |
| 7,326,194 B2 | 2/2008 | Zinger et al. |
| 7,344,385 B2 | 3/2008 | Chen |
| 7,364,570 B2 | 4/2008 | Gerondale et al. |
| 7,377,912 B2 | 5/2008 | Graf et al. |
| 7,390,312 B2 | 6/2008 | Barrelle |
| 7,390,314 B2 | 6/2008 | Stutz et al. |
| 7,407,493 B2 | 8/2008 | Cane |
| 7,418,880 B1 | 9/2008 | Smith |
| D578,210 S | 10/2008 | Muta et al. |
| 7,442,186 B2 | 10/2008 | Blomquist |
| 7,455,663 B2 | 11/2008 | Bikovsky |
| 7,465,290 B2 | 12/2008 | Reilly |
| 7,468,055 B2 | 12/2008 | Prais et al. |
| 7,488,181 B2 | 2/2009 | Van |
| 7,497,842 B2 | 3/2009 | Diaz et al. |
| 7,500,963 B2 | 3/2009 | Westbye et al. |
| 7,501,587 B2 | 3/2009 | English |
| 7,503,786 B2 | 3/2009 | Kato et al. |
| 7,530,964 B2 | 5/2009 | Lavi et al. |
| 7,540,858 B2 | 6/2009 | Dibiasi |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| 7,597,682 B2 | 10/2009 | Moberg |
| D604,835 S | 11/2009 | Conley |
| 7,611,491 B2 | 11/2009 | Pickhard |
| 7,621,893 B2 | 11/2009 | Moberg et al. |
| 7,628,770 B2 | 12/2009 | Ethelfeld |
| 7,628,772 B2 | 12/2009 | Mcconnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,658,734 B2 | 2/2010 | Adair et al. |
| 7,660,627 B2 | 2/2010 | Mcnichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,903 B2 | 5/2010 | Estes et al. |
| 7,717,913 B2 | 5/2010 | Novak et al. |
| 7,722,574 B2 | 5/2010 | Toman et al. |
| 7,736,333 B2 | 6/2010 | Gillespie, III |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,758,548 B2 | 7/2010 | Gillespie et al. |
| 7,758,550 B2 | 7/2010 | Bollenbach et al. |
| 7,766,867 B2 | 8/2010 | Lynch et al. |
| 7,766,873 B2 | 8/2010 | Moberg et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,794,426 B2 | 9/2010 | Briones et al. |
| 7,794,427 B2 | 9/2010 | Estes et al. |
| 7,801,599 B2 | 9/2010 | Young et al. |
| 7,806,868 B2 | 10/2010 | De et al. |
| 7,828,528 B2 | 11/2010 | Estes et al. |
| 7,837,659 B2 | 11/2010 | Bush et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,892,206 B2 | 2/2011 | Moberg et al. |
| 7,901,382 B2 | 3/2011 | Daily et al. |
| 7,905,867 B2 | 3/2011 | Veasey et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,976,514 B2 | 7/2011 | Abry et al. |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 7,998,131 B2 | 8/2011 | Adair et al. |
| 8,002,754 B2 | 8/2011 | Kawamura et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,034,026 B2 | 10/2011 | Grant et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,062,255 B2 | 11/2011 | Brunnberg et al. |
| 8,062,257 B2 | 11/2011 | Moberg et al. |
| 8,065,096 B2 | 11/2011 | Moberg et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,105,293 B2 | 1/2012 | Pickhard |
| 8,114,046 B2 | 2/2012 | Covino et al. |
| 8,114,064 B2 | 2/2012 | Alferness et al. |
| 8,114,066 B2 | 2/2012 | Naef et al. |
| 8,118,781 B2 | 2/2012 | Knopper et al. |
| 8,121,603 B2 | 2/2012 | Zhi |
| D657,462 S | 4/2012 | Siroky |
| 8,147,446 B2 | 4/2012 | Yodfat et al. |
| 8,151,169 B2 | 4/2012 | Bieth et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinaenen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,177,749 B2 | 5/2012 | Slate et al. |
| 8,182,447 B2 | 5/2012 | Moberg et al. |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,257,345 B2 | 9/2012 | Adair et al. |
| 8,267,893 B2 | 9/2012 | Moberg et al. |
| 8,267,921 B2 | 9/2012 | Yodfat et al. |
| 8,273,061 B2 | 9/2012 | McConnell et al. |
| 8,287,520 B2 | 10/2012 | Drew et al. |
| 8,292,647 B1 | 10/2012 | Mcgrath et al. |

(56) References Cited

U.S. PATENT DOCUMENTS

| | | |
|---|---|---|
| 8,303,572 B2 | 11/2012 | Adair et al. |
| 8,308,679 B2 | 11/2012 | Hanson et al. |
| 8,308,695 B2 | 11/2012 | Laiosa |
| 8,323,250 B2 | 12/2012 | Chong et al. |
| 8,348,898 B2 | 1/2013 | Cabiri |
| 8,366,668 B2 | 2/2013 | Maritan |
| 8,372,039 B2 | 2/2013 | Mernoe et al. |
| 8,373,421 B2 | 2/2013 | Lindegger et al. |
| 8,409,141 B2 | 4/2013 | Johansen et al. |
| 8,409,142 B2 | 4/2013 | Causey et al. |
| 8,409,143 B2 | 4/2013 | Lanigan et al. |
| 8,409,149 B2 | 4/2013 | Hommann et al. |
| 8,414,533 B2 | 4/2013 | Alexandersson |
| 8,414,557 B2 | 4/2013 | Istoc et al. |
| 8,425,468 B2 | 4/2013 | Weston |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente et al. |
| 8,475,408 B2 | 7/2013 | Mernoe et al. |
| 8,479,595 B2 | 7/2013 | Vazquez et al. |
| 8,483,980 B2 | 7/2013 | Moberg et al. |
| 8,490,790 B2 | 7/2013 | Cocheteux et al. |
| 8,495,918 B2 | 7/2013 | Bazargan et al. |
| 8,496,862 B2 | 7/2013 | Zelkovich et al. |
| 8,500,716 B2 | 8/2013 | Adair et al. |
| 8,512,287 B2 | 8/2013 | Cindrich et al. |
| 8,512,295 B2 | 8/2013 | Evans et al. |
| 8,517,987 B2 | 8/2013 | Istoc et al. |
| 8,517,992 B2 | 8/2013 | Jones |
| 8,523,803 B1 | 9/2013 | Favreau |
| 8,551,046 B2 | 10/2013 | Causey et al. |
| 8,556,856 B2 | 10/2013 | Bazargan et al. |
| 8,562,364 B2 | 10/2013 | Lin et al. |
| 8,568,361 B2 | 10/2013 | Yodfat et al. |
| 8,574,216 B2 | 11/2013 | Istoc et al. |
| 8,603,026 B2 | 12/2013 | Favreau |
| 8,603,027 B2 | 12/2013 | Favreau |
| 8,603,028 B2 | 12/2013 | Mudd et al. |
| 8,617,110 B2 | 12/2013 | Moberg et al. |
| 8,622,966 B2 | 1/2014 | Causey et al. |
| 8,628,510 B2 | 1/2014 | Bazargan et al. |
| 8,632,499 B2 | 1/2014 | Grant et al. |
| 8,647,074 B2 | 2/2014 | Moberg et al. |
| 8,647,296 B2 | 2/2014 | Moberg et al. |
| 8,647,303 B2 | 2/2014 | Cowe |
| 8,668,672 B2 | 3/2014 | Moberg et al. |
| 8,674,288 B2 | 3/2014 | Hanson et al. |
| 8,679,060 B2 | 3/2014 | Mernoe et al. |
| 8,681,010 B2 | 3/2014 | Moberg et al. |
| D702,834 S | 4/2014 | Norton et al. |
| 8,690,855 B2 | 4/2014 | Alderete et al. |
| 8,708,961 B2 | 4/2014 | Field et al. |
| 8,715,237 B2 | 5/2014 | Moberg et al. |
| 8,721,603 B2 | 5/2014 | Lundquist |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian et al. |
| 8,777,896 B2 | 7/2014 | Starkweather et al. |
| 8,777,924 B2 | 7/2014 | Kanderian et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,784,378 B2 | 7/2014 | Weinandy |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,845,587 B2 | 9/2014 | Lanigan et al. |
| 8,858,508 B2 | 10/2014 | Lavi et al. |
| 8,864,739 B2 | 10/2014 | Moberg et al. |
| 8,876,770 B2 | 11/2014 | Kraft et al. |
| 8,876,778 B2 | 11/2014 | Carrel |
| 8,911,410 B2 | 12/2014 | Ekman et al. |
| 8,915,882 B2 | 12/2014 | Cabiri |
| 8,915,886 B2 | 12/2014 | Cowe |
| 8,920,374 B2 | 12/2014 | Bokelman et al. |
| 8,932,266 B2 | 1/2015 | Wozencroft |
| 8,979,802 B2 | 3/2015 | Woehr |
| 8,986,250 B2 | 3/2015 | Beebe et al. |
| 9,011,164 B2 | 4/2015 | Filman et al. |
| 9,011,371 B2 | 4/2015 | Moberg et al. |
| 9,011,387 B2 | 4/2015 | Ekman et al. |
| 9,033,925 B2 | 5/2015 | Moberg et al. |
| 9,061,104 B2 | 6/2015 | Daniel |
| 9,061,110 B2 | 6/2015 | Avery et al. |
| 9,072,827 B2 | 7/2015 | Cabiri |
| 9,072,845 B2 | 7/2015 | Hiles |
| 9,089,475 B2 | 7/2015 | Fangrow |
| 9,089,641 B2 | 7/2015 | Kavazov |
| 9,107,999 B2 | 8/2015 | Moberg et al. |
| 9,138,534 B2 | 9/2015 | Yodfat et al. |
| 9,149,575 B2 | 10/2015 | Cabiri |
| 9,173,996 B2 | 11/2015 | Gray et al. |
| 9,173,997 B2 | 11/2015 | Gross et al. |
| 9,180,248 B2 | 11/2015 | Moberg et al. |
| 9,205,188 B2 | 12/2015 | Lanigan et al. |
| 9,205,199 B2 | 12/2015 | Kemp et al. |
| D747,799 S | 1/2016 | Norton et al. |
| 9,233,215 B2 | 1/2016 | Hourmand et al. |
| 9,259,532 B2 | 2/2016 | Cabiri |
| 9,283,327 B2 | 3/2016 | Hourmand et al. |
| 9,308,318 B2 | 4/2016 | Lanigan et al. |
| 9,308,327 B2 | 4/2016 | Marshall et al. |
| 9,314,569 B2 | 4/2016 | Causey et al. |
| 9,320,849 B2 | 4/2016 | Smith et al. |
| 9,327,073 B2 | 5/2016 | Moberg et al. |
| 9,339,607 B2 | 5/2016 | Langley et al. |
| 9,345,834 B2 | 5/2016 | Henley et al. |
| 9,345,836 B2 | 5/2016 | Cabiri et al. |
| 9,350,634 B2 | 5/2016 | Fadell |
| 9,352,090 B2 | 5/2016 | Brereton et al. |
| 9,364,606 B2 | 6/2016 | Cindrich et al. |
| 9,364,608 B2 | 6/2016 | Moberg et al. |
| 9,381,300 B2 | 7/2016 | Smith et al. |
| 9,393,365 B2 | 7/2016 | Cabiri |
| 9,421,323 B2 | 8/2016 | Cabiri et al. |
| 9,421,337 B2 | 8/2016 | Kemp et al. |
| 9,427,531 B2 | 8/2016 | Hourmand et al. |
| 9,433,732 B2 | 9/2016 | Moberg et al. |
| 9,433,733 B2 | 9/2016 | Moberg et al. |
| 9,446,188 B2 | 9/2016 | Grant et al. |
| 9,446,196 B2 | 9/2016 | Hourmand et al. |
| 9,452,261 B2 | 9/2016 | Alon |
| 9,463,280 B2 | 10/2016 | Cabiri |
| 9,463,889 B2 | 10/2016 | Schmitz et al. |
| 9,468,720 B2 | 10/2016 | Mudd et al. |
| 9,474,859 B2 | 10/2016 | Ekman et al. |
| 9,492,622 B2 | 11/2016 | Brereton et al. |
| 9,522,234 B2 | 12/2016 | Cabiri |
| 9,539,384 B2 | 1/2017 | Servansky |
| 9,539,388 B2 | 1/2017 | Causey et al. |
| 9,539,757 B2 | 1/2017 | Ramirez et al. |
| 9,572,926 B2 | 2/2017 | Cabiri |
| 9,572,927 B2 | 2/2017 | Bruggemann et al. |
| 9,579,452 B2 | 2/2017 | Adair et al. |
| 9,579,471 B2 | 2/2017 | Carrel et al. |
| 9,610,407 B2 | 4/2017 | Bruggemann et al. |
| 9,656,019 B2 | 5/2017 | Cabiri et al. |
| 9,656,021 B2 | 5/2017 | Brereton et al. |
| 9,656,025 B2 | 5/2017 | Bostrom et al. |
| 9,707,356 B2 | 7/2017 | Hourmand et al. |
| 9,744,306 B2 | 8/2017 | Cowe |
| 9,775,948 B2 | 10/2017 | Bechmann et al. |
| 9,782,545 B2 | 10/2017 | Gross et al. |
| 9,789,247 B2 | 10/2017 | Kamen et al. |
| 9,814,830 B2 | 11/2017 | Mernoe et al. |

(56) References Cited

U.S. PATENT DOCUMENTS

| | | |
|---|---|---|
| 9,814,839 B2 | 11/2017 | Eaton |
| 9,849,242 B2 | 12/2017 | Henley et al. |
| 9,862,519 B2 | 1/2018 | Deutschle et al. |
| 9,999,722 B2 | 6/2018 | Yodfat et al. |
| 10,010,681 B2 | 7/2018 | Koch et al. |
| 10,076,356 B2 | 9/2018 | Hadvary et al. |
| 10,143,794 B2 | 12/2018 | Lanigan et al. |
| 10,149,943 B2 | 12/2018 | Bar-El et al. |
| D838,367 S | 1/2019 | Norton et al. |
| 10,166,335 B2 | 1/2019 | Reber et al. |
| 10,207,048 B2 | 2/2019 | Gray et al. |
| 10,207,051 B2 | 2/2019 | Cereda et al. |
| 10,227,161 B2 | 3/2019 | Auerbach |
| 10,232,116 B2 | 3/2019 | Ekman et al. |
| 10,258,740 B2 | 4/2019 | McLoughlin et al. |
| 10,376,641 B2 | 8/2019 | Hirschel et al. |
| 10,376,647 B2 | 8/2019 | Farris et al. |
| 10,434,262 B2 | 10/2019 | Bendek et al. |
| 10,500,352 B2 | 12/2019 | Grant et al. |
| 10,561,798 B2 | 2/2020 | Holland et al. |
| 10,576,213 B2 | 3/2020 | Gylleby |
| 10,576,220 B2 | 3/2020 | Armes |
| 10,583,260 B2 | 3/2020 | Kemp |
| 10,603,430 B2 | 3/2020 | Shor et al. |
| 10,722,645 B2 | 7/2020 | Kamen et al. |
| 10,729,847 B2 | 8/2020 | Gray et al. |
| 10,758,679 B2 | 9/2020 | Bar-El et al. |
| 10,842,942 B2 | 11/2020 | Iibuchi et al. |
| 11,027,059 B2 | 6/2021 | Niklaus et al. |
| 2001/0005781 A1 | 6/2001 | Bergens et al. |
| 2001/0018937 A1 | 9/2001 | Nemoto |
| 2001/0025168 A1 | 9/2001 | Gross et al. |
| 2001/0034502 A1 | 10/2001 | Moberg et al. |
| 2001/0041869 A1 | 11/2001 | Causey et al. |
| 2002/0010423 A1 | 1/2002 | Gross et al. |
| 2002/0016569 A1 | 2/2002 | Critchlow et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0055718 A1 | 5/2002 | Hunt |
| 2002/0065488 A1 | 5/2002 | Suzuki et al. |
| 2002/0107487 A1 | 8/2002 | Preuthun |
| 2002/0120186 A1 | 8/2002 | Keimel |
| 2002/0123740 A1 | 9/2002 | Flaherty et al. |
| 2002/0151855 A1 | 10/2002 | Douglas et al. |
| 2002/0161332 A1 | 10/2002 | Ramey |
| 2002/0169215 A1 | 11/2002 | Meng |
| 2002/0173748 A1 | 11/2002 | McConnell et al. |
| 2002/0173769 A1 | 11/2002 | Gray et al. |
| 2003/0009133 A1 | 1/2003 | Ramey |
| 2003/0014018 A1 | 1/2003 | Giambattista et al. |
| 2003/0050602 A1 | 3/2003 | Pettis et al. |
| 2003/0069518 A1 | 4/2003 | Daley et al. |
| 2003/0125671 A1 | 7/2003 | Aramata et al. |
| 2003/0130618 A1 | 7/2003 | Gray et al. |
| 2003/0135159 A1 | 7/2003 | Daily et al. |
| 2003/0160683 A1 | 8/2003 | Blomquist |
| 2003/0167039 A1 | 9/2003 | Moberg |
| 2003/0171717 A1 | 9/2003 | Farrugia et al. |
| 2003/0199825 A1 | 10/2003 | Flaherty et al. |
| 2003/0216683 A1 | 11/2003 | Shekalim |
| 2003/0236498 A1 | 12/2003 | Gross et al. |
| 2004/0000818 A1 | 1/2004 | Preuthun et al. |
| 2004/0003493 A1 | 1/2004 | Adair et al. |
| 2004/0010207 A1 | 1/2004 | Flaherty et al. |
| 2004/0049160 A1 | 3/2004 | Hsieh et al. |
| 2004/0049161 A1 | 3/2004 | Shearn |
| 2004/0082911 A1 | 4/2004 | Tiu et al. |
| 2004/0092873 A1 | 5/2004 | Moberg |
| 2004/0116866 A1 | 6/2004 | Gorman et al. |
| 2004/0122359 A1 | 6/2004 | Wenz et al. |
| 2004/0122369 A1 | 6/2004 | Schriver et al. |
| 2004/0127857 A1 | 7/2004 | Shemesh et al. |
| 2004/0135078 A1 | 7/2004 | Mandro et al. |
| 2004/0158172 A1 | 8/2004 | Hancock |
| 2004/0158205 A1 | 8/2004 | Savage |
| 2004/0186419 A1 | 9/2004 | Cho |
| 2004/0186441 A1 | 9/2004 | Graf et al. |
| 2004/0210196 A1 | 10/2004 | Bush et al. |
| 2004/0260233 A1 | 12/2004 | Garibotto et al. |
| 2005/0027255 A1 | 2/2005 | Lavi et al. |
| 2005/0033234 A1 | 2/2005 | Sadowski et al. |
| 2005/0038391 A1 | 2/2005 | Wittland et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0124940 A1 | 6/2005 | Martin et al. |
| 2005/0154353 A1 | 7/2005 | Alheidt |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197626 A1 | 9/2005 | Moberg et al. |
| 2005/0197650 A1 | 9/2005 | Sugimoto et al. |
| 2005/0203461 A1 | 9/2005 | Flaherty et al. |
| 2005/0238507 A1 | 10/2005 | Diianni et al. |
| 2005/0245956 A1 | 11/2005 | Steinemann et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0036216 A1 | 2/2006 | Rimlinger et al. |
| 2006/0095010 A1 | 5/2006 | Westbye |
| 2006/0095014 A1 | 5/2006 | Ethelfeld |
| 2006/0122577 A1 | 6/2006 | Poulsen et al. |
| 2006/0124269 A1 | 6/2006 | Miyazaki et al. |
| 2006/0173406 A1 | 8/2006 | Hayes et al. |
| 2006/0173439 A1 | 8/2006 | Thorne et al. |
| 2006/0184154 A1 | 8/2006 | Moberg et al. |
| 2006/0195029 A1 | 8/2006 | Shults et al. |
| 2006/0206054 A1 | 9/2006 | Shekalim |
| 2006/0206057 A1 | 9/2006 | Deruntz et al. |
| 2006/0211982 A1 | 9/2006 | Prestrelski et al. |
| 2006/0229569 A1 | 10/2006 | Lavi et al. |
| 2006/0264888 A1 | 11/2006 | Moberg et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0025879 A1 | 2/2007 | Vandergaw |
| 2007/0049865 A1 | 3/2007 | Radmer et al. |
| 2007/0073228 A1 | 3/2007 | Mernoe et al. |
| 2007/0079894 A1 | 4/2007 | Kraus et al. |
| 2007/0118405 A1 | 5/2007 | Campbell et al. |
| 2007/0167912 A1 | 7/2007 | Causey et al. |
| 2007/0179444 A1 | 8/2007 | Causey et al. |
| 2007/0185449 A1 | 8/2007 | Mernoe |
| 2007/0197954 A1 | 8/2007 | Keenan |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0265568 A1 | 11/2007 | Tsals et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097326 A1 | 4/2008 | Moberg et al. |
| 2008/0097381 A1 | 4/2008 | Moberg et al. |
| 2008/0097387 A1* | 4/2008 | Spector .............. A61C 5/62 604/512 |
| 2008/0108951 A1 | 5/2008 | Jerde et al. |
| 2008/0140006 A1 | 6/2008 | Eskuri et al. |
| 2008/0140014 A1 | 6/2008 | Miller et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |

(56) References Cited

U.S. PATENT DOCUMENTS

| | | |
|---|---|---|
| 2008/0208138 A1 | 8/2008 | Lim et al. |
| 2008/0215006 A1 | 9/2008 | Thorkild |
| 2008/0215013 A1 | 9/2008 | Felix-Faure |
| 2008/0215015 A1 | 9/2008 | Cindrich et al. |
| 2008/0221523 A1 | 9/2008 | Moberg et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319383 A1 | 12/2008 | Byland et al. |
| 2008/0319416 A1 | 12/2008 | Yodat et al. |
| 2009/0012478 A1 | 1/2009 | Weston |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076383 A1 | 3/2009 | Toews et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093763 A1 | 4/2009 | Gonnelli et al. |
| 2009/0093792 A1* | 4/2009 | Gross .............. A61M 5/158 604/218 |
| 2009/0093793 A1 | 4/2009 | Gross et al. |
| 2009/0105650 A1 | 4/2009 | Wiegel et al. |
| 2009/0105663 A1 | 4/2009 | Brand et al. |
| 2009/0124977 A1 | 5/2009 | Jensen |
| 2009/0143730 A1 | 6/2009 | De et al. |
| 2009/0143735 A1 | 6/2009 | De et al. |
| 2009/0149830 A1 | 6/2009 | Spector |
| 2009/0182277 A1 | 7/2009 | Carter |
| 2009/0182284 A1 | 7/2009 | Morgan |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299288 A1 | 12/2009 | Sie et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0010455 A1 | 1/2010 | Elahi et al. |
| 2010/0018334 A1 | 1/2010 | Lessing |
| 2010/0030156 A1 | 2/2010 | Beebe et al. |
| 2010/0030198 A1 | 2/2010 | Beebe et al. |
| 2010/0049128 A1 | 2/2010 | Mckenzie et al. |
| 2010/0049144 A1 | 2/2010 | Mcconnell et al. |
| 2010/0057057 A1 | 3/2010 | Hayter et al. |
| 2010/0076382 A1 | 3/2010 | Weston |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0160894 A1 | 6/2010 | Julian et al. |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0241103 A1 | 9/2010 | Kraft et al. |
| 2010/0256486 A1 | 10/2010 | Savage |
| 2010/0264931 A1 | 10/2010 | Lindegger et al. |
| 2010/0268169 A1 | 10/2010 | Llewellyn-Hyde et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1 | 3/2011 | Cabiri |
| 2011/0092915 A1 | 4/2011 | Olson et al. |
| 2011/0112504 A1 | 5/2011 | Causey et al. |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178463 A1 | 7/2011 | Cabiri |
| 2011/0178472 A1 | 7/2011 | Cabiri |
| 2011/0201998 A1 | 8/2011 | Pongpairochana et al. |
| 2011/0224616 A1 | 9/2011 | Slate et al. |
| 2011/0224646 A1 | 9/2011 | Yodfat et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022496 A1 | 1/2012 | Causey et al. |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041387 A1 | 2/2012 | Bruggemann et al. |
| 2012/0041414 A1 | 2/2012 | Estes et al. |
| 2012/0071828 A1 | 3/2012 | Tojo et al. |
| 2012/0096953 A1 | 4/2012 | Bente et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0109059 A1 | 5/2012 | Ranalletta et al. |
| 2012/0118777 A1 | 5/2012 | Kakiuchi et al. |
| 2012/0123387 A1 | 5/2012 | Gonzalez et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0172817 A1 | 7/2012 | Brüggemann et al. |
| 2012/0184917 A1 | 7/2012 | Bom et al. |
| 2012/0226234 A1 | 9/2012 | Bazargan et al. |
| 2012/0238961 A1 | 9/2012 | Julian et al. |
| 2012/0259282 A1 | 10/2012 | Alderete et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0131589 A1 | 5/2013 | Mudd et al. |
| 2013/0131604 A1 | 5/2013 | Avery |
| 2013/0133438 A1 | 5/2013 | Kow et al. |
| 2013/0172808 A1 | 7/2013 | Gilbert |
| 2013/0190693 A1 | 7/2013 | Ekman et al. |
| 2013/0200549 A1 | 8/2013 | Felts et al. |
| 2013/0204187 A1 | 8/2013 | Avery et al. |
| 2013/0204191 A1 | 8/2013 | Cindrich et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |

(56) References Cited

U.S. PATENT DOCUMENTS

| | | |
|---|---|---|
| 2013/0245604 A1 | 9/2013 | Kouyoumjian et al. |
| 2013/0253419 A1 | 9/2013 | Favreau |
| 2013/0253420 A1 | 9/2013 | Favreau |
| 2013/0253421 A1 | 9/2013 | Favreau |
| 2013/0253434 A1 | 9/2013 | Cabiri |
| 2013/0267895 A1 | 10/2013 | Hemmingsen |
| 2013/0296799 A1 | 11/2013 | Degtiar et al. |
| 2013/0296824 A1 | 11/2013 | Mo et al. |
| 2013/0304021 A1 | 11/2013 | Cabiri et al. |
| 2013/0310753 A1 | 11/2013 | Cabiri |
| 2013/0310807 A1 | 11/2013 | Adair et al. |
| 2013/0323699 A1 | 12/2013 | Edwards et al. |
| 2013/0331791 A1 | 12/2013 | Gross et al. |
| 2013/0338584 A1 | 12/2013 | Mounce et al. |
| 2014/0018735 A1 | 1/2014 | Causey et al. |
| 2014/0031747 A1 | 1/2014 | Ardehali |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0121633 A1 | 5/2014 | Causey et al. |
| 2014/0128807 A1 | 5/2014 | Moberg et al. |
| 2014/0128835 A1 | 5/2014 | Moberg et al. |
| 2014/0135692 A1 | 5/2014 | Alderete et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete et al. |
| 2014/0163526 A1 | 6/2014 | Cabiri et al. |
| 2014/0171881 A1 | 6/2014 | Cabiri |
| 2014/0174223 A1 | 6/2014 | Gross et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0207104 A1 | 7/2014 | Vouillamoz et al. |
| 2014/0213975 A1 | 7/2014 | Clemente et al. |
| 2014/0214001 A1 | 7/2014 | Mortazavi |
| 2014/0228768 A1 | 8/2014 | Eggert et al. |
| 2014/0236087 A1 | 8/2014 | Alderete et al. |
| 2014/0243786 A1 | 8/2014 | Gilbert et al. |
| 2014/0261758 A1 | 9/2014 | Wlodarczyk et al. |
| 2014/0343503 A1 | 11/2014 | Holmqvist |
| 2014/0364808 A1 | 12/2014 | Niklaus et al. |
| 2015/0005703 A1 | 1/2015 | Hutchinson et al. |
| 2015/0073344 A1 | 3/2015 | Van Damme et al. |
| 2015/0088071 A1 | 3/2015 | Cabiri |
| 2015/0112278 A1 | 4/2015 | Ray et al. |
| 2015/0119798 A1 | 4/2015 | Gross et al. |
| 2015/0157788 A1* | 6/2015 | Gescheit ............. G16H 20/17 604/67 |
| 2015/0157806 A1 | 6/2015 | Knutsson |
| 2015/0202375 A1 | 7/2015 | Schabbach et al. |
| 2015/0374926 A1 | 12/2015 | Gross et al. |
| 2016/0030665 A1 | 2/2016 | Cabiri |
| 2016/0051756 A1 | 2/2016 | Cabiri |
| 2016/0144117 A1 | 5/2016 | Chun |
| 2016/0151586 A1 | 6/2016 | Kemp |
| 2016/0175515 A1 | 6/2016 | Mccullough |
| 2016/0184512 A1 | 6/2016 | Marbet et al. |
| 2016/0193406 A1 | 7/2016 | Cabiri |
| 2016/0199590 A1 | 7/2016 | Schabbach et al. |
| 2016/0213840 A1 | 7/2016 | Schabbach et al. |
| 2016/0220755 A1 | 8/2016 | Lanigan et al. |
| 2016/0228652 A1 | 8/2016 | Cabiri et al. |
| 2016/0296713 A1 | 10/2016 | Schader et al. |
| 2016/0296716 A1 | 10/2016 | Cabiri et al. |
| 2016/0331900 A1 | 11/2016 | Wei |
| 2016/0339168 A1 | 11/2016 | Hutchinson et al. |
| 2016/0346478 A1 | 12/2016 | Bar-El et al. |
| 2016/0354553 A1 | 12/2016 | Anderson et al. |
| 2017/0007774 A1 | 1/2017 | Brockmeier |
| 2017/0043092 A1 | 2/2017 | Murakami et al. |
| 2017/0058349 A1 | 3/2017 | Levy et al. |
| 2017/0175859 A1 | 6/2017 | Brockmeier |
| 2017/0246399 A1 | 8/2017 | Forlani et al. |
| 2017/0246403 A1 | 8/2017 | Cowe et al. |
| 2018/0028765 A1 | 2/2018 | Waller et al. |
| 2018/0133413 A1 | 5/2018 | Grant et al. |
| 2018/0214637 A1 | 8/2018 | Kemp et al. |
| 2018/0304029 A1 | 10/2018 | Koch et al. |
| 2019/0022306 A1 | 1/2019 | Gibson et al. |
| 2019/0060578 A1 | 2/2019 | Farris et al. |
| 2019/0071217 A1 | 3/2019 | Brown et al. |
| 2019/0099549 A1 | 4/2019 | Lanigan et al. |
| 2019/0175821 A1 | 6/2019 | Kamen et al. |
| 2019/0224415 A1 | 7/2019 | Dugand et al. |
| 2019/0240417 A1 | 8/2019 | Hostettler et al. |
| 2019/0328968 A1 | 10/2019 | Giambattista |
| 2020/0009323 A1 | 1/2020 | Nair et al. |
| 2020/0164151 A1 | 5/2020 | Farris et al. |
| 2020/0215270 A1 | 7/2020 | Ogawa et al. |
| 2020/0297929 A1 | 9/2020 | Zhang |
| 2020/0360602 A1 | 11/2020 | Gray et al. |
| 2021/0138157 A1 | 5/2021 | Bar-El et al. |
| 2021/0220551 A1 | 7/2021 | Dowd et al. |

FOREIGN PATENT DOCUMENTS

| | | |
|---|---|---|
| CN | 1863566 A | 11/2006 |
| CN | 101090749 A | 12/2007 |
| CN | 101227943 A | 7/2008 |
| CN | 101448536 A | 6/2009 |
| CN | 101522235 A | 9/2009 |
| CN | 101541362 A | 9/2009 |
| CN | 101641126 A | 2/2010 |
| CN | 201692438 U | 1/2011 |
| CN | 201941304 U | 8/2011 |
| CN | 102186733 A | 9/2011 |
| CN | 102378638 A | 3/2012 |
| CN | 105102025 A | 11/2015 |
| DE | 0855313 C | 11/1952 |
| DE | 1064693 B | 9/1959 |
| DE | 19518807 A1 | 12/1995 |
| DE | 19717107 A1 | 11/1998 |
| EP | 0017412 A1 | 10/1980 |
| EP | 0222656 A1 | 5/1987 |
| EP | 0401179 A1 | 12/1990 |
| EP | 0851774 A1 | 7/1998 |
| EP | 0925082 A1 | 6/1999 |
| EP | 1003581 A1 | 5/2000 |
| EP | 1124600 A1 | 8/2001 |
| EP | 1219312 A2 | 7/2002 |
| EP | 1472477 A1 | 11/2004 |
| EP | 1530979 A1 | 5/2005 |
| EP | 1666080 A1 | 6/2006 |
| EP | 1372762 B1 | 2/2007 |
| EP | 1974759 A1 | 10/2008 |
| EP | 2060606 A1 | 5/2009 |
| EP | 2140897 A1 | 1/2010 |
| EP | 2173413 A1 | 4/2010 |
| EP | 2185227 A2 | 5/2010 |
| EP | 2192935 A1 | 6/2010 |
| EP | 2361648 A1 | 8/2011 |
| EP | 2364739 A1 | 9/2011 |
| EP | 2393534 A1 | 12/2011 |
| EP | 2452708 A1 | 5/2012 |
| EP | 2498589 A1 | 9/2012 |
| EP | 2574355 A1 | 4/2013 |
| EP | 2393535 B1 | 3/2015 |
| EP | 2878321 A1 | 6/2015 |
| EP | 2886144 A1 | 6/2015 |
| EP | 1904130 B1 | 3/2016 |
| EP | 2991705 A1 | 3/2016 |
| EP | 3266478 A1 | 1/2018 |
| EP | 2007455 B1 | 3/2019 |
| EP | 2819724 B1 | 3/2019 |
| FR | 2770136 A1 | 4/1999 |
| GB | 2436526 A | 10/2007 |
| JP | 62-112566 A | 5/1987 |
| JP | 01-172843 U | 12/1989 |

(56) References Cited

FOREIGN PATENT DOCUMENTS

| | | |
|---|---|---|
| JP | 05-062828 A | 3/1993 |
| JP | 07-194701 A | 8/1995 |
| JP | 3035448 U | 3/1997 |
| JP | 09-505758 A | 6/1997 |
| JP | 11-507260 A | 6/1999 |
| JP | 2000-107289 A | 4/2000 |
| JP | 2000-515394 A | 11/2000 |
| JP | 2001-512992 A | 8/2001 |
| JP | 2002-505601 A | 2/2002 |
| JP | 2002-507459 A | 3/2002 |
| JP | 2002-528676 A | 9/2002 |
| JP | 2003-501157 A | 1/2003 |
| JP | 2003-534061 A | 11/2003 |
| JP | 2004-501721 A | 1/2004 |
| JP | 2004-512100 A | 4/2004 |
| JP | 2003-527138 A | 8/2005 |
| JP | 2005-523127 A | 8/2005 |
| JP | 2005-527249 A | 9/2005 |
| JP | 2005-270629 A | 10/2005 |
| JP | 2006-507067 A | 3/2006 |
| JP | 2006-510450 A | 3/2006 |
| JP | 2006-525046 A | 11/2006 |
| JP | 2007-509661 A | 4/2007 |
| JP | 2007-306990 A | 11/2007 |
| JP | 2008-534131 A | 8/2008 |
| JP | 2008-220961 A | 9/2008 |
| JP | 2009-502273 A | 1/2009 |
| JP | 2009-101093 A | 5/2009 |
| JP | 2010-501281 A | 1/2010 |
| JP | 2010-540054 A | 12/2010 |
| JP | 2010-540156 A | 12/2010 |
| JP | 2011-136153 A | 7/2011 |
| JP | 2012-100927 A | 5/2012 |
| JP | 4947871 B2 | 6/2012 |
| JP | 2013-500811 A | 1/2013 |
| JP | 2013-505433 A | 2/2013 |
| JP | 2013-517095 A | 5/2013 |
| JP | 2013-519473 A | 5/2013 |
| JP | 2013-530778 A | 8/2013 |
| JP | 2013-531520 A | 8/2013 |
| JP | 2013-531540 A | 8/2013 |
| JP | 2014-030489 A | 2/2014 |
| JP | 2014-515669 A | 7/2014 |
| JP | 2014-518743 A | 8/2014 |
| JP | 2014-521443 A | 8/2014 |
| JP | 2014-525339 A | 9/2014 |
| JP | 2015-514486 A | 5/2015 |
| JP | 2016-525428 A | 8/2016 |
| JP | 2016-530016 A | 9/2016 |
| WO | 90/09202 A1 | 8/1990 |
| WO | 93/07922 A1 | 4/1993 |
| WO | 94/07553 A1 | 4/1994 |
| WO | 94/15660 A1 | 7/1994 |
| WO | 95/13838 A1 | 5/1995 |
| WO | 96/09083 A1 | 3/1996 |
| WO | 96/32975 A1 | 10/1996 |
| WO | 97/00091 A1 | 1/1997 |
| WO | 97/10012 A1 | 3/1997 |
| WO | 97/21457 A1 | 6/1997 |
| WO | 97/33638 A1 | 9/1997 |
| WO | 98/57683 A1 | 12/1998 |
| WO | 98/57686 A1 | 12/1998 |
| WO | 99/29151 A1 | 6/1999 |
| WO | 99/38554 A1 | 8/1999 |
| WO | 99/59665 A1 | 11/1999 |
| WO | 00/25844 A1 | 5/2000 |
| WO | 00/69509 A1 | 11/2000 |
| WO | 01/30415 A2 | 5/2001 |
| WO | 01/30421 A2 | 5/2001 |
| WO | 01/70304 A1 | 9/2001 |
| WO | 01/72357 A2 | 10/2001 |
| WO | 01/87384 A1 | 11/2001 |
| WO | 01/89607 A2 | 11/2001 |
| WO | 01/89613 A1 | 11/2001 |
| WO | 02/02165 A2 | 1/2002 |
| WO | 02/04049 A1 | 1/2002 |
| WO | 02/34315 A1 | 5/2002 |
| WO | 02/38204 A2 | 5/2002 |
| WO | 02/56934 A2 | 7/2002 |
| WO | 02/56943 A2 | 7/2002 |
| WO | 02/72182 A1 | 9/2002 |
| WO | 03/62672 A1 | 7/2003 |
| WO | 03/90833 A1 | 11/2003 |
| WO | 2004/000397 A1 | 12/2003 |
| WO | 2004/032990 A2 | 4/2004 |
| WO | 2004/098684 A2 | 11/2004 |
| WO | 2004/105841 A1 | 12/2004 |
| WO | 2005/018703 A2 | 3/2005 |
| WO | 2005/037350 A2 | 4/2005 |
| WO | 2005/070485 A1 | 8/2005 |
| WO | 2005/072795 A2 | 8/2005 |
| WO | 2006/018617 A1 | 2/2006 |
| WO | 2006/037434 A1 | 4/2006 |
| WO | 2006/052737 A1 | 5/2006 |
| WO | 2006/069380 A1 | 6/2006 |
| WO | 2006/102676 A1 | 9/2006 |
| WO | 2006/104806 A2 | 10/2006 |
| WO | 2006/121921 A2 | 11/2006 |
| WO | 2007/017052 A1 | 2/2007 |
| WO | 2007/051563 A1 | 5/2007 |
| WO | 2007/056504 A1 | 5/2007 |
| WO | 2007/066152 A2 | 6/2007 |
| WO | 2007/073228 A1 | 6/2007 |
| WO | 2007/119178 A2 | 10/2007 |
| WO | 2008/001377 A2 | 1/2008 |
| WO | 2008/014908 A1 | 2/2008 |
| WO | 2008/057976 A2 | 5/2008 |
| WO | 2008/072229 A2 | 6/2008 |
| WO | 2008/076459 A1 | 6/2008 |
| WO | 2008/078318 A2 | 7/2008 |
| WO | 2009/019438 A1 | 2/2009 |
| WO | 2009/022132 A2 | 2/2009 |
| WO | 2009/043000 A1 | 4/2009 |
| WO | 2009/043564 A1 | 4/2009 |
| WO | 2009/044401 A2 | 4/2009 |
| WO | 2009/046989 A2 | 4/2009 |
| WO | 2009/069064 A1 | 6/2009 |
| WO | 2009/125398 A2 | 10/2009 |
| WO | 2009/144085 A2 | 12/2009 |
| WO | 2010/078227 A1 | 7/2010 |
| WO | 2010/078242 A1 | 7/2010 |
| WO | 2010/089313 A1 | 8/2010 |
| WO | 2011/075105 A1 | 6/2011 |
| WO | 2011/090955 A1 | 7/2011 |
| WO | 2011/090956 A2 | 7/2011 |
| WO | 2011/101378 A1 | 8/2011 |
| WO | 2011/110872 A1 | 9/2011 |
| WO | 2011/124631 A1 | 10/2011 |
| WO | 2011/129175 A1 | 10/2011 |
| WO | 2011/131778 A1 | 10/2011 |
| WO | 2011/131780 A2 | 10/2011 |
| WO | 2011/131781 A1 | 10/2011 |
| WO | 2011/133823 A1 | 10/2011 |
| WO | 2011/156373 A1 | 12/2011 |
| WO | 2012/003221 A1 | 1/2012 |
| WO | 2012/032411 A2 | 3/2012 |
| WO | 2012/040528 A1 | 3/2012 |
| WO | 2012/145752 A2 | 10/2012 |
| WO | 2012/160157 A1 | 11/2012 |
| WO | 2012/168691 A1 | 12/2012 |
| WO | 2013/036602 A1 | 3/2013 |
| WO | 2013/058697 A1 | 4/2013 |
| WO | 2013/115843 A1 | 8/2013 |
| WO | 2014/132293 A1 | 9/2014 |
| WO | 2014/179117 A1 | 11/2014 |
| WO | 2014/179774 A1 | 11/2014 |
| WO | 2014/194183 A2 | 12/2014 |
| WO | 2015/048791 A1 | 4/2015 |
| WO | 2015/048803 A2 | 4/2015 |
| WO | 2015/078868 A1 | 6/2015 |
| WO | 2015/091758 A1 | 6/2015 |
| WO | 2015/091850 A1 | 6/2015 |
| WO | 2015/114158 A1 | 8/2015 |
| WO | 2015/114428 A1 | 8/2015 |

(56) References Cited

FOREIGN PATENT DOCUMENTS

| | | |
|---|---|---|
| WO | 2015/118358 A1 | 8/2015 |
| WO | 2015/163009 A1 | 10/2015 |
| WO | 2016/087626 A1 | 6/2016 |
| WO | 2016/087627 A1 | 6/2016 |
| WO | 2016/141082 A1 | 9/2016 |
| WO | 2017/022639 A1 | 2/2017 |
| WO | 2017/161076 A1 | 9/2017 |
| WO | 2018/222521 A1 | 12/2018 |
| WO | 2019/224782 A1 | 11/2019 |
| WO | 2020/120087 A1 | 6/2020 |
| WO | 2020/193468 A1 | 10/2020 |

OTHER PUBLICATIONS

Office Action dated Jun. 9, 2017 in EP Application No. 14166591.9.
Office Action dated Jun. 9, 2017 in EP Application No. 14166596.8.
Office Action dated Mar. 1, 2018 in EP Application No. 14166592.7.
Office Action dated Mar. 10, 2015 in CN Application No. 201180006567.4.
Office Action dated Mar. 10, 2015 in U.S. Appl. No. 12/244,666 by Gross.
Office Action dated Mar. 10, 2015 in U.S. Appl. No. 13/643,470 by Alon.
Office Action dated Mar. 30, 2018 in U.S. Appl. No. 14/850,450 by Gross.
Office Action dated Mar. 31, 2015 in JP Application No. 2012-550068.
Office Action dated Mar. 5, 2014 in CN Application No. 200880117084.X.
Office Action dated May 1, 2015 in U.S. Appl. No. 14/638,525 by Filman.
Office Action dated May 13, 2015 in CN Application No. 201380025566.3.
Office Action dated May 14, 2018 in EP Application No. 08808111.2.
Office Action dated May 16, 2012 in U.S. Appl. No. 12/615,828.
Office Action dated May 18, 2018 in EP 14166591.9.
Office Action dated May 23, 2014 in U.S. Appl. No. 13/472,112 by Cabiri.
Office Action dated May 24, 2017 in U.S. Appl. No. 13/874,121, by Degtiar.
Office Action dated May 25, 2021 in Japanese Office Action 2018-538073.
Office Action dated May 3, 2012 in CN Application No. 200880117084.X.
Office Action dated May 31, 2016 in U.S. Appl. No. 14/593,051 by Gross.
Office Action dated May 4, 2017 in CN Application No. 2014101836665.
Office Action dated May 5, 2015 in CN Application No. 201180006571.0.
Office Action dated May 7, 2015 in JP Application No. 2012-550069.
Office Action dated Nov. 10, 2016 in U.S. Appl. No. 13/874,121, by Degtiar.
Office Action dated Nov. 13, 2017 in U.S. Appl. No. 14/193,692, by Gross.
Office Action dated Nov. 2, 2014 in CN Application No. 201180006571.0.
Office Action dated Nov. 21, 2014 in U.S. Appl. No. 13/429,840 by Cabiri.
Office Action dated Nov. 21, 2014 in U.S. Appl. No. 13/472,112 by Cabiri.
Office Action dated Nov. 25, 2016 in U.S. Appl. No. 13/874,017, by Cabiri.
Office Action dated Nov. 4, 2013 in EP Application No. 11 709 234.6.
Office Action dated Nov. 5, 2013 in JP Application No. 2010-527595.
Office Action dated Nov. 5, 2014 in U.S. Appl. No. 13/643,470 by Alon.
Office Action dated Nov. 8, 2017 in U.S. Appl. No. 13/874,121, by Degtiar.
Office Action dated Oct. 13, 2020 in Japanese Application No. 2018-538073.
Office Action dated Oct. 2, 2018 in JP Application No. 2018-535062 (Year: 2018).
Office Action dated Oct. 28, 2011 in U.S. Appl. No. 12/615,828.
Office Action dated Oct. 28, 2016 in CN Application No. 2014101783742.
Office Action dated Oct. 5, 2016 in U.S. Appl. No. 13/964,651, by Gross.
Office Action dated Oct. 6, 2017 in U.S. Appl. No. 14/861,478, by Cabiri.
Office Action dated Oct. 9, 2014 in U.S. Appl. No. 13/873,335.
Office Action dated Sep. 18, 2015 in U.S. Appl. No. 13/874,085 by Cabiri.
Office Action dated Sep. 2, 2010 in U.S. Appl. No. 12/244,688 by Gross.
Office Action dated Sep. 2, 2014 in JP Application No. 2012-550068.
Office Action dated Sep. 2, 2014 in JP Application No. 2012-550069.
Office Action dated Sep. 28, 2017 in IN Application No. 2528/DELNP/2010.
Office Action dated Sep. 29, 2013 in CN Application No. 201080040968.7.
Office Action dated Sep. 30, 2010 in U.S. Appl. No. 12/689,250, by Cabiri.
Office Action dated Sep. 30, 2015 in U.S. Appl. No. 13/667,739 by Cabiri.
Office Action dated Sep. 6, 2011 in U.S. Appl. No. 12/345,818.
Office Action dated Sep. 9, 2015 in U.S. Appl. No. 13/643,470 by Alon.
Office Action dated Aug. 17, 2021 in Indian Application No. 201827027625.
Communication Pursuant to Rules 161 and 162 dated Apr. 6, 2018 in EP Application No. 16784688.0.
Copaxone(Registered), Innovative Drugs, Teva Pharmaceuticals, downloaded from webpage: http://levapharm.com/copaxone/, Download date: Jan. 2009, original posting date: unknown, 3 pages.
Daikyo Crystal Zenith(Registered) polymer, Manufactured by Daikyo Seiko, Lid. (Jun. 25, 2008).
Definition of Monolithic. In Merriam-Webster's online dictionary. Retrieved from https://www.merriam-webster.com/dictionary/monolithic (Year: 2021).
English translation of an Office Action dated Jan. 30, 2013 in CN Application No. 200880117084.X.
English translation of an Office Action dated Mar. 5, 2014 in CN Application No. 200880117084.X.
European Search Report (Partial) dated Mar. 8, 2017 in EP Application 16193157.1.
Extended European Search Report dated Aug. 7, 2014 in EP Application No. 1417477.4.
Extended European Search Report dated Feb. 12, 2018 in EP Application No. 17191756.0.
Extended European Search Report dated Feb. 13, 2017 in EP Application No. 16171626.1.
Extended European Search Report dated Feb. 23, 2015 in EP Application No. 14166591.9.
Extended European Search Report dated Feb. 23, 2015 in EP Application No. 14166596.8.
Extended European Search Report dated Jul. 3, 2017 in EP Application No. 16190054.3.
Extended European Search Report dated Mar. 27, 2014 in EP Application No. 14154717.4.
Extended European Search Report dated Mar. 8, 2016 in EP Application No. 14166592.7.
Extended European Search Report dated Nov. 10, 2016 in EP Application No. 08808111.2.
Extended European Search Report dated Jul. 28, 2020 in European Application No. 20172466.3.

(56) References Cited

OTHER PUBLICATIONS

Extended Search Report dated Aug. 7, 2014 in EP Application No. 14171477.4.
Extended Search Report dated Jul. 7, 2017 in EP Application No. 16193157.1.
Int'l Preliminary Report on Patentability dated Nov. 22, 2017 in Int'l Application No. PCT/US2016/068371.
Int'l Search Report and Written Opinion dated Jan. 12, 2011 in Int'l Application No. PCT/US2010/048556; Written Opinion.
Int'l Search Report and Written Opinion dated Jan. 26, 2017 in Int'l Application No. PCT/US2016/056213.
Int'l Search Report and Written Opinion dated Mar. 27, 2017 in Int'l Application No. PCT/US2016/056247.
Int'l Search Report and Written Opinion dated Apr. 21, 2017 in Int'l Application No. PCT/US2016/068367.
Int'l Search Report and Written Opinion dated May 15, 2017 in Int'l Application No. PCT/US2016/068371.
Int'l Search Report and Written Opinion dated Jul. 6, 2017 in Int'l Application No. PCT/US2017/022966.
Int'l Search Report and Written Opinion dated Nov. 28, 2016 in Int'l Application No. PCT/US2016/056218.
Int'l Search Report and Written Opinion dated Dec. 2, 2016 in Int'l Application No. PCT/US2016/056210.
Int'l Search Report and Written Opinion dated Dec. 5, 2016 in Int'l Application No. PCT/US2016/056233.
Int'l Search Report and Written Opinion dated Dec. 8, 2016 in Inl'l Application No. PCT/US2016/056227.
Int'l Search Report and Written Opinion dated Dec. 15, 2016 in Inl'l Application No. PCT/US2016/056258.
Int'l Search Repport (Partial), dated Dec. 20, 2016 in Int'l Application No. PCT/US2016/056247.
Int'l Preliminary Report on Patentability dated Jan. 8, 2018 in Int'l Application No. PCT/US2016/056218.
Int'l Preliminary Report on Patentability dated Apr. 7, 2010 in Int'l Application No. PCT/IL2008/001312.
Int'l Preliminary Report on Patentability dated Aug. 2, 2012 in Int'l Application No. PCT/US2011/021604.
Int'l Preliminary Report on Patentability dated Feb. 7, 2013 in Int'l Application No. PCT/US11/21605.
Int'l Preliminary Report on Patentability dated Jan. 18, 2018 in Int'l Application No. PCT/US2016/056210.
Int'l Preliminary Report on Patentability dated Jan. 18, 2018 in Int'l Application No. PCT/US2016/056213.
Int'l Preliminary Report on Patentability dated Jan. 18, 2018 in Int'l Application No. PCT/US2016/056223.
Int'l Preliminary Report on Patentability dated Jan. 18, 2018 in Int'l Application No. PCT/US2016/056227.
Int'l Preliminary Report on Patentability dated Jul. 16, 2015 in Int'l Application No. PCT/US2013/078040.
Int'l Preliminary Report on Patentability dated May 14, 2015 in Int'l Application No. PCT/US2013/065211.
Int'l Preliminary Report on Patentability dated Nov. 27, 2014 in Int'l Application No. PCT/US2013/039465.
Int'l Preliminary Report on Patentability dated Nov. 30, 2017 in Int'l Application No. PCT/US2016/068367.
Int'l Preliminary Report on Patentability dated Nov. 9, 2018 in Int'l Application No. PCT/US2016/056238.
Int'l Preliminary Report on Patentability dated Oct. 9, 2014 in Int'l Application No. PCT/US2013/033118.
Int'l Preliminary Report on Patentability dated Sep. 1, 2011 in Int'l Application No. PCT/US2010/048556.
Int'l Search Report and Written Opinion dated Apr. 3, 2014 in Int'l Application No. PCT/US2013/078040.
Int'l Search Report and Written Opinion dated Aug. 5, 2013 in Int'l Application No. PCT/US2013/033118.
Int'l Search Report and Written Opinion dated Jan. 7, 2014 in Int'l Application No. PCT/US2013/065211.
Office Action dated Feb. 20, 2015 in U.S. Appl. No. 13/521,181 by Cabiri.
Office Action dated Nov. 6, 2015 in U.S. Appl. No. 14/715,791 by Cabiri.
Office Action dated Oct. 6, 2020 in Japanese Application No. 2018-538527.
Partial European Search Report dated Nov. 24, 2015 in EP Application No. 14166592.7.
Search Report dated Oct. 14, 2016 in CN Application No. 2014101783742.
U.S. Appl. No. 12/559,563, filed Sep. 15, 2009.
U.S. Appl. No. 12/689,249, filed Jan. 19, 2010.
U.S. Appl. No. 12/689,250, filed Jan. 19, 2010.
U.S. Appl. No. 13/429,840 by Cabiri, filed Mar. 26, 2012.
U.S. Appl. No. 13/472,112 by Cabiri, filed May 15, 2012.
U.S. Appl. No. 13/521,167 by Cabiri, filed Jul. 9, 2012.
U.S. Appl. No. 13/521,181 by Cabiri, filed Jul. 9, 2012.
U.S. Appl. No. 13/643,470 by Alon, filed Oct. 25, 2012.
U.S. Appl. No. 13/733,516 by Cabiri, filed Jan. 3, 2013.
U.S. Appl. No. 13/873,335 by Filman, filed Apr. 30, 2013.
U.S. Appl. No. 13/874,017 by Cabiri, filed Apr. 30, 2013.
U.S. Appl. No. 13/874,085 by Cabiri, filed Apr. 30, 2013.
U.S. Appl. No. 13/874,121 by Degtiar, filed Apr. 30, 2013.
U.S. Appl. No. 13/892,905 by Cabiri, filed May 13, 2013.
U.S. Appl. No. 13/964,651 by Gross, filed Aug. 12, 2013.
U.S. Appl. No. 14/193,692 by Gross, filed Feb. 28, 2014.
U.S. Appl. No. 14/258,661 by Cabiri, filed Apr. 22, 2014.
U.S. Appl. No. 14/553,399 by Cabiri, filed Nov. 25, 2014.
U.S. Appl. No. 14/593,051 by Gross, filed Jan. 9, 2015.
U.S. Appl. No. 14/638,525 by Filman, filed Mar. 4, 2015.
U.S. Appl. No. 14/683,193 by Cabiri, filed Apr. 10, 2015.
U.S. Appl. No. 14/715,791 by Cabiri, filed May 19, 2015.
U.S. Appl. No. 14/725,009 by Bar-El, filed May 29, 2015.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
U.S. Appl. No. 29/479,307 by Norton, filed Jan. 14, 2014.
U.S. Appl. No. 60/997,459, filed Oct. 2, 2007.
West Introduces the Daikyo Crystal Zenith RU Prefillable Syringe, Pharmaceutical Online, Jun. 2008, downloaded from webpage: http://www.pharmaceuticalonline.com/article.mvc/west-introduces-prefillab- le-syringe-system, Download date: Jan. 2009, original posting date: Jun. 2008, 2 pages.
Int'l Search Report and Written Opinion dated Jul. 12, 2017 in Int'l Application No. PCT/US2016/056238.
Int'l Search Report and Written Opinion dated Jul. 26, 2013 in Int'l Application No. PCT/US2012/039465.
Int'l Search Report and Written Opinion dated Jul. 31, 2014 in Int'l Application No. PCT/US2014/033598.
Int'l Search Report and Written Opinion dated May 13, 2009 in Int'l Application No. PCT/IL2008/001312.
Int'l Search Report dated Apr. 26, 2010 in Int'l Application No. PCT/US2009/069552.
Int'l Search Report dated Jun. 17, 2011 in Int'l Application No. PCT/US2011/021604.
Int'l Search Report dated Oct. 12, 2011 in Int'l Application No. PCT/US11/21605.
Int'l Search Report dated Sep. 22, 2011 in Int'l Application No. PCT/IL11/00368; Written Opinion.
Int'l Written Opinion dated Jul. 19, 2012 in Int'l Application No. PCT/US11/21605.
Inte'l Search Report and Written Opinion dated Nov. 30, 2016 in Int'l Application No. PCT/US2016/056223.
International Preliminary Report on Patentability and Written Opinion dated Jul. 5, 2011 in International Application No. PCT/US2009/069552.
Notice of Allowance dated Aug. 24, 2015 in U.S. Appl. No. 29/479,307 by Norton.
Offce Action dated Sep. 21, 2010 in U.S. Appl. No. 12/244,666 by Gross.
Office Action dated Apr. 22, 2016 in CN Application No. 2014102892041.
Office Action dated Apr. 5, 2010 in U.S. Appl. No. 12/244,666 by Gross.

(56) References Cited

OTHER PUBLICATIONS

Office Action dated Apr. 5, 2010 in U.S. Appl. No. 12/244,688 by Gross.
Office Action dated Aug. 13, 2015 in U.S. Appl. No. 14/553,399 by Cabiri.
Office Action dated Aug. 14, 2017 in CN Application No. 201410178318.9.
Office Action dated Aug. 15, 2013 in CN Application No. 200880117084.X.
Office Action dated Aug. 26, 2014 in CN Application No. 201180006567.4.
Office Action dated Aug. 6, 2014 in EP Appl. No. 11 707 942.6.
Office Action dated Dec. 1, 2015 in CN Application No. 201410289204.1.
Office Action dated Dec. 10, 2013 in CN Application No. 201180006567.4.
Office Action dated Dec. 15, 2017 in U.S. Appl. No. 15/269,248, by Cabiri.
Office Action dated Dec. 17, 2013 in JP Application No. 2012-529808.
Office Action dated Dec. 4, 2017 in CN Application No. 201410178374.2.
Office Action dated Dec. 9, 2016 in U.S. Appl. No. 14/593,051, by Gross.
Office Action dated Feb. 16, 2017 in CN Application No. 2014101783189.
Office Action dated Feb. 21, 2012 in U.S. Appl. No. 12/689,249.
Office Action dated Feb. 24, 2015 in U.S. Appl. No. 14/258,661 by Cabiri.
Office Action dated Feb. 24, 2017 in U.S. Appl. No. 13/964,651, by Gross.
Office Action dated Feb. 28, 2014 in CN Application No. 201180006571.0.
Office Action dated Feb. 4, 2014 in EP Application No. 11 707 942.6.
Office Action dated Jan. 10, 2017 in U.S. Appl. No. 14/193,692, by Gross.
Office Action dated Jan. 30, 2013 in CN Application No. 200880117084.X.
Office Action dated Jan. 8, 2013 in JP Application No. 2010-527595.
Office Action dated Jan. 8, 2014 in U.S. Appl. No. 13/521,167 by Cabiri.
Office Action dated Jul. 13, 2011 in U.S. Appl. No. 12/559,563 by Cabiri.
Office Action dated Jul. 2, 2012 in U.S. Appl. No. 13/272,555 by Cabiri.
Office Action dated Jul. 28, 2020 in Japanese Application No. 2018-538074.
Office Action dated Jul. 3, 2017 in CN Application No. 2014101783742.
Office Action dated Jul. 31, 2015 in U.S. Appl. No. 13/521,181 by Cabiri.
Office Action dated Jul. 7, 2014 in U.S. Appl. No. 12/244,666 by Gross.
Office Action dated Jun. 10, 2016 in U.S. Appl. No. 13/964,651 by Gross.
Office Action dated Jun. 14, 2018 in U.S. Appl. No. 13/874,121, by Degtiar.
Office Action dated Jun. 2, 2016 in CN Application No. 2014101783189.
Office Action dated Jun. 3, 2014 in JP Application No. 2010-527595.
Office Action dated Jun. 4, 2015 in U.S. Appl. No. 13/667,739 by Cabiri.

* cited by examiner

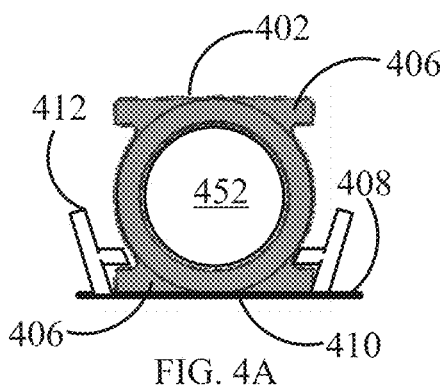
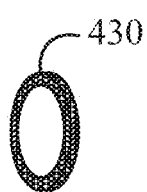
FIG. 4H
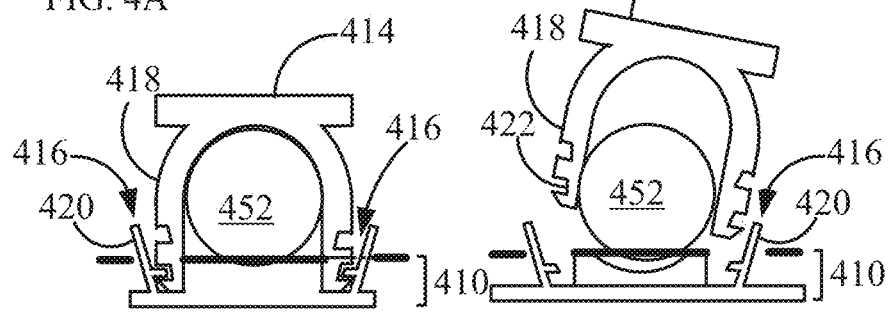
FIG. 4B    FIG. 4C
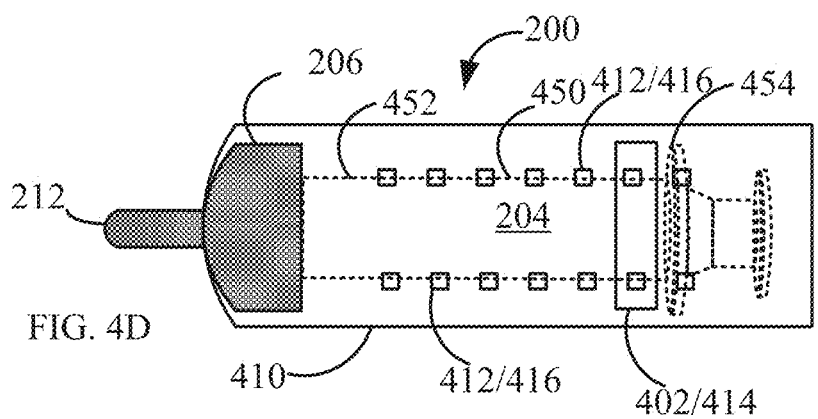
FIG. 4D
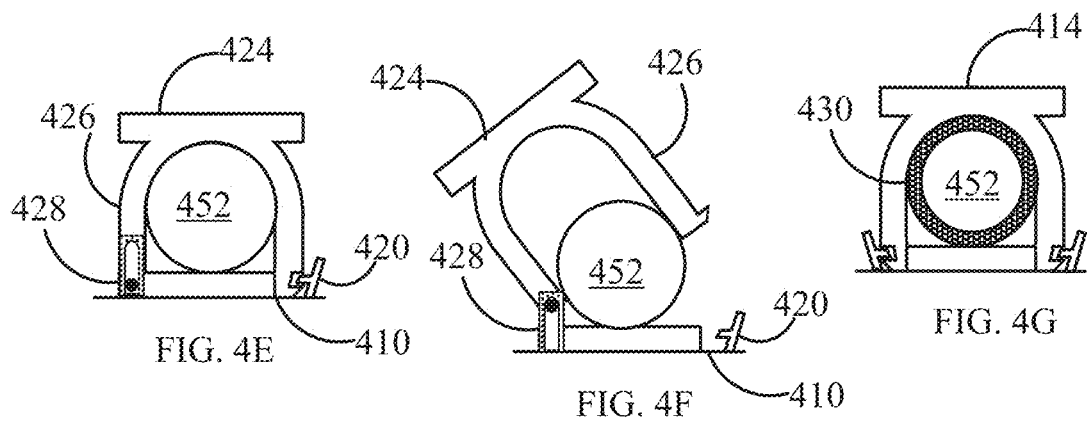
FIG. 4E    FIG. 4F    FIG. 4G

BENT FLUID PATH ADD ON TO A PREFILLED RESERVOIR

CROSS-REFERENCE TO RELATED APPLICATIONS

This application is a divisional of co-pending U.S. application Ser. No. 15/766,719, filed Apr. 6, 2018, which is a section 371 of International Application No. PCT/US16/56213, filed Oct. 10, 2016, which was published Apr. 13, 2017 under International Publication No. WO 2017/062931 A1, which is a continuation of U.S. application Ser. No. 15/204,542, filed Jul. 7, 2016 and issued as U.S. Pat. No. 10,576,207 on Mar. 3, 2020, which claims the benefit of U.S. Provisional Application No. 62/281,536, filed Jan. 21, 2016 and U.S. Provisional Application No. 62/284,806, filed Oct. 9, 2015; and a continuation of U.S. application Ser. No. 15/269,248, filed Sep. 19, 2016, the disclosures of which are incorporated herein by reference.

FIELD AND BACKGROUND OF THE INVENTION

The present invention, in some embodiments thereof, relates to a self-injector and, more particularly, but not exclusively, to a patch self-injector.

A subcutaneous (SC) injection is a method of administering medication under the skin, commonly into fatty tissue between the skin and the muscle. The current trend toward subcutaneous injection for biologicals using auto-injectors such as, for example, reusable and disposable pens, auto-injectors, and patch injectors that adhere to the surface of the skin gives users the freedom to self-inject at home.

In many cases, reformulated drugs can be more concentrated, at times more viscous and the desired injection volume greater than 1 mL. For high viscosity products, delivery in under 10 seconds can lead to painful injections, which may result in users failing to follow their treatment regimen. It may be difficult at times for a user to keep a Pen or any other upright injector stationary and at a correct angle of injection during injections for periods of over 10 seconds or several minutes. Patch auto or self-injectors for self-administered SC injections are therefore becoming more common.

Additional background art includes U.S. Pat. Nos. 6,843,782 and 5,858,001.

SUMMARY OF THE INVENTION

According to an aspect of some embodiments of the present invention there is provided an add-on for a self-injector including an adaptor including at least one coupling sized and shaped to couple the adaptor to a fluid reservoir, a bent fluid path configured at a first end to penetrate tissue and coupled at a second end to the adaptor and wherein the add-on coupled to the fluid reservoir forms an integral self-injector cartridge unit configured to be sterilized and filled with an injectable.

According to some embodiments of the invention, the add-on includes a needle protective cap. According to some embodiments the fluid path is bent at a 90 degree angle. According to some embodiments, the add-on further includes at least one fastener sized and fitted to couple the body of the reservoir to a self-injector.

According to an aspect of some embodiments of the present invention there is provided an add-on for a self-injector including an adaptor including at least one coupling sized and shaped to couple the adaptor to a fluid reservoir, a bent fluid path configured at a first end to penetrate tissue and coupled at a second end to the adaptor and wherein when the add-on is coupled to the fluid reservoir sterile fluid communication is secured between the reservoir and the first end of the bent fluid path. According to some embodiments of the invention, the bent fluid path includes a coupling at the second end sized and shaped to couple the bent fluid path to the adaptor and secure sterile fluid communication in-between. According to some embodiments of the invention, the add-on further includes at least one fastener sized and fitted to couple the body of the reservoir to a self-injector. According to some embodiments of the invention, the bent fluid path includes a hollow needle. According to some embodiments of the invention, the fluid path is bent at a 90 degree angle.

According to some embodiments of the invention, the reservoir is a prefilled cartridge. According to some embodiments of the invention, the reservoir is a syringe. According to some embodiments of the invention, the reservoir is a vial. According to some embodiments of the invention, at least a portion of the reservoir is made of glass. According to some embodiments of the invention, at least a portion of the reservoir is made of a plastic material. According to some embodiments of the invention, the add-on is sterilizable en bloc. According to some embodiments of the invention, the adaptor coupling is a Leur lock coupling. According to some embodiments of the invention, the adaptor coupling is a vial adaptor. According to some embodiments of the invention, the adaptor coupling is a slide-on fluid reservoir coupling. According to some embodiments of the invention, the adaptor further includes a coupling sized and shaped to couple the add-on to a self-injector.

According to an aspect of some embodiments of the present invention there is provided an add-on for a self-injector, including at least one adaptor including at least one bent fluid path and sized and fitted to sterilely couple the bent fluid path to at least a tip of a fluid reservoir, and at least one fastener sized and fitted to a body of the fluid reservoir to the self-injector, and wherein the adaptor and the fastener are configured to couple to the self-injector at least one of a plurality of reservoirs having different sizes and tip types.

According to some embodiments of the invention, the distance between the adaptor and the fastener is adjustable. According to some embodiments of the invention, the internal diameter of the fastener is adjustable. According to some embodiments of the invention, the add-on further includes a fitting sized and shaped to fit along the inner circumference of the fastener. According to some embodiments of the invention, the fitting reduces the inner diameter of the fastener. According to some embodiments of the invention, at least a portion of the fastener is made of a plastic material. According to some embodiments of the invention, at least a portion of the fluid reservoir is made of glass. According to some embodiments of the invention, at least a portion of the fluid reservoir is made of a plastic material. According to some embodiments of the invention, the bent fluid path includes a hollow needle. According to some embodiments of the invention, the fluid path is bent at a 90 degree angle.

According to some embodiments of the invention, the reservoir is a prefilled cartridge. According to some embodiments of the invention, the reservoir is a fluid reservoir. According to some embodiments of the invention, the reservoir is a vial. According to some embodiments of the invention, add-on is sterilizable en bloc. According to some embodiments of the invention, the adaptor coupling is a Leur lock coupling. According to some embodiments of the invention, the adaptor coupling is a vial adaptor. According to some embodiments of the invention, the adaptor coupling is a slide-on fluid reservoir coupling. According to some embodiments of the invention, the adaptor further includes a coupling sized and shaped to couple the add-on to a self-injector.

According to an aspect of some embodiments of the present invention there is provided an add-on to a self-injector coupling system, including a self-injector including a support plate with a plurality of attachment points, at least one adaptor including at least one bent fluid path and sized and fitted to sterilely couple the bent fluid path to at least a tip of a fluid reservoir and at least one fastener sized and fitted to couple to a body of the fluid reservoir and to at least one of the attachment points.

According to some embodiments of the invention, the adaptor is sized and fitted to couple to at least one of the attachment points. According to some embodiments of the invention, the attachment points are distributed on the support plate at varying distances from the adaptor. According to some embodiments of the invention, the varying distances correspond to varying lengths of the fluid reservoir. According to some embodiments of the invention, the internal diameter of the fastener is adjustable. According to some embodiments of the invention, the system further includes a fitting sized and shaped to fit along the inner circumference of the fastener. According to some embodiments of the invention, the fitting reduces the inner diameter of the fastener.

According to an aspect of some embodiments of the present invention there is provided a self-injector kit, including at least one self-injector including a support plate with a plurality of attachment points, a plurality of adaptors including at least one bent fluid path and sized and fitted to sterilely couple the bent fluid path to at least a tip of at least one type of fluid reservoir and a plurality of fasteners sized and fitted to couple to at least one diameter of a body of the fluid reservoir and to at least one of the attachment points.

According to some embodiments of the invention, at least one fitting is sized and shaped to fit along the inner circumference of at least one of the plurality of fasteners. According to some embodiments of the invention, the fitting reduces the inner diameter of the fastener. According to some embodiments of the invention, the fluid reservoir is at least one of a prefilled cartridge, a syringe and a vial. According to some embodiments of the invention, at least a portion of the fluid reservoir is made of glass. According to some embodiments of the invention, at least a portion of the fastener is made of a plastic material. According to some embodiments of the invention, at least one of the adaptors is sterile.

According to an aspect of some embodiments of the present invention there is provided a method of assembling an add-on for a self-injector including: selecting an empty fluid reservoir, forming a self-injector cartridge unit by coupling at least a tip of the fluid reservoir to an adaptor including at least one bent fluid path and sized and fitted to fluidly couple the bent fluid path to at least a tip of the fluid reservoir and establishing fluid communication between the fluid reservoir and the bent fluid path.

According to some embodiments of the invention, the method further includes sterilizing the cartridge, filling the fluid reservoir with a sterile injectable, inserting a plunger into a non-bent fluid path end of the fluid reservoir and sterilely sealing the end of the fluid reservoir. According to some embodiments of the invention, the method further includes selecting at least one fastener and coupling the fastener to a body of the fluid reservoir and coupling the fastener to at least one corresponding attachment point on the injector.

According to an aspect of some embodiments of the present invention there is provided a method of coupling an add-on for a self-injector to a fluid reservoir including: selecting a fluid reservoir, coupling at least a tip of the fluid reservoir to an adaptor including at least one bent fluid path and sized and fitted to fluidly couple the bent fluid path to at least a tip of the fluid reservoir and establishing sterile communication between the fluid reservoir and the bent fluid path.

According to some embodiments of the invention, the method further includes selecting at least one fastener and coupling the fastener to a body of the fluid reservoir and coupling the fastener to at least one corresponding attachment point on the injector.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL
VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-4H are plan and perspective view simplified illustration of exemplary embodiments of a modular fluid reservoir-injector coupling system;

Figure 1:
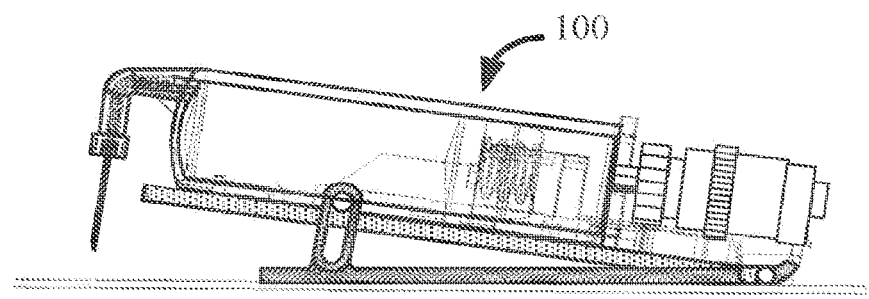
FIG. 1 is a side view simplified illustration of a patch type self-injector.

DESCRIPTION OF SPECIFIC EMBODIMENTS
OF THE INVENTION

The present invention, in some embodiments thereof, relates to self-injectors and, more particularly, but not exclusively, to a patch self-injector.

An aspect of some embodiments of the invention relates to a self-injector sized and fitted to couple fluid reservoirs of variable sizes and tip types to the injector. In some embodiments, the self-injector comprises at least a needle-bearing portion and at least one fastener attachable to the injector and at least to a barrel of a fluid reservoir. In some embodiments, the needle bearing portion comprises a needle protective cap. In some embodiments, the self-injector and the fluid reservoir are provided sterile. For example, the reservoir, needle bearing portion and cap may be assembled and sterilized together. In some embodiments, the self-injector and the fluid reservoir are provided unsterile. In some embodiments, the self-injector and the fluid reservoir are sterilized prior to filling with an injectable. In some embodiments, post sterilization the sterile fluid reservoir is filled with an injectable and provided sterilely sealed and capped with a protective cap. In some embodiments, the distance between the needle-bearing portion and the fastener is adjustable. In some embodiments, the internal radius of the fastener is adjustable. In some embodiments, the injector comprises a patch type self-injector. In some embodiments, the injector comprises a bent needle. In some embodiments, the needle is bent at a 90 degree angle. In some embodiments, at least one portion of the injector comprises at least a bore sized and fitted to accommodate a fluid reservoir tip. In some embodiments, at least a portion of the needle extends through the bore. In some embodiments, the needle-bearing portion is fixed in place. In some embodiments the fluid reservoir comprises a syringe. In some embodiments, the fluid reservoir comprises a vial. In some embodiments the fluid reservoir comprises a prefilled cartridge.

In some embodiments, the self-injector is sized and fitted to accommodate refillable fluid reservoirs. In some embodiments, a self-injector is sized and fitted to accommodate prefilled fluid reservoirs. In some embodiments the prefilled fluid reservoir tips are sealed for sterility. In some embodiments, the injector comprises one or more adaptors that couple the needle to one or more fluid reservoir tip types. In some embodiments, the adaptor is sized and fitted for coupling the needle to a slip or push-on type fluid reservoir tip. In some embodiments, the adaptor is sized and fitted for coupling the needle to a Luer-lock type fluid reservoir tip. In some embodiments, the adaptor is sized and fitted for coupling the needle to a catheter type fluid reservoir tip. In some embodiments, the adaptor is sized and fitted for coupling the needle to a fluid reservoir with a centered tip. In some embodiments, the adaptor is sized and fitted for coupling the needle to a fluid reservoir with an eccentric tip.

An aspect of some embodiments of the invention relates to a self-injector comprising a modular fluid reservoir-injector coupling system. In some embodiments, the modular system comprises a support plate sized and fitted to accommodate variable types and sizes of fluid reservoirs. In some embodiments, the injector comprises a bent needle. In some embodiments, the needle is bent at a 90 degree angle. In some embodiments, the support plater comprises one or more notches configured to accommodate fasteners that fix the fluid reservoir to the injector. In some embodiments, at least a portion of one or more fasteners is fixedly coupled to a self-injector support plate. In some embodiments, at least a portion of one or more fasteners is releasably coupled to the self-injector support plate. In some embodiments, one or more fasteners comprises at least an aperture sized and fitted to accommodate a fluid reservoir tip. In some embodiments, at least one fastener comprises a bent needle. In some embodiments, at least one fastener comprises at least a bore sized and fitted to accommodate a fluid reservoir tip. In some embodiments, at least a portion of the needle extends through the aperture or bore.

In some embodiments, at least one fastener comprises a latch and a hinge. In some embodiments, at least one fastener comprises one or more latches. In some embodiments, at least one fastener is sized and fitted to fasten a barrel of a fluid reservoir. In some embodiments, at least one fastener is sized and fitted to fasten a finger flange of a fluid reservoir. In some embodiments, at least one fastener comprises at least one fitting sized and fitted for a specific fluid reservoir barrel diameter. In some embodiments, at least one fastener is fitted with an at least partially resilient pad. In some embodiments, at least a portion of a fluid reservoir is urged against the resilient pad when locked into place in the injector. In some embodiments, the resilient pad stops leaks from the fluid reservoir tip-needle coupling. In some embodiments, the resilient pad comprises an aperture for a tip of a needle.

An aspect of some embodiments of the invention relates to a self-injector comprising a bent needle and having a Luer-lock coupling sized and fitted to receive a fluid reservoir with a male Luer-lock type tip. In some embodiments, the Luer-lock coupling comprises a cylinder coupled at one end to the injector and comprising a tabbed rim configured to screw into a male Leur-lock fluid reservoir tip. In some embodiments, at least a portion of the bent needle is disposed in a lumen of the cylinder. In some embodiments, at least a portion of the needle is attached to the inside wall of the cylinder. In some embodiments, at least a portion of the cylinder lumen between the portion of the needle and the inside wall comprises a seal. In some embodiments, at least one end of the bent needle extends beyond the cylinder tabbed rim. In some embodiments, the end of the bent needle extending beyond the cylinder tabbed rim comprises a protective sheath. In some embodiments, the protective sheath maintains sterility of the needle end. In some embodiments, the protective sheath maintains sterility of the portion of the needle inside the cylinder lumen up to and including the end of the needle extending beyond the tabbed rim. In some embodiments, upon coupling, the rim of the male luer lock urges the protective sheath against the tip of the needle. In some embodiments, the needle tip ruptures the protective sheath urged against the needle tip by the male luer lock rim.

An aspect of some embodiments of the invention relates to a self-injector sized and fitted to sterilely accommodate variable types and sizes of fluid reservoirs. In some embodiments, the self-injector comprises a coupling that maintains sterility of a pathway of an injectable during and after coupling to a fluid reservoir containing the injectable. In some embodiments, the injector coupling comprises an end of a needle at least partially isolated by at least one protective sheath. In some embodiments, during coupling a tip of a coupled fluid reservoir urges at least one sheath against the needle end rupturing the protective sheath. In some embodiments, a tip of a coupled fluid reservoir comprises a sealing membrane over an opening in the tip. In some embodiments, during coupling the injector needle is urged against the membrane and penetrates the fluid reservoir tip.

An aspect of some embodiments of the invention relates to a self-injector kit comprising a support plate and a plurality of fasteners and fittings sized and fitted to attach to the support plate. In some embodiments, the plurality of fasteners and fittings sized and fitted to sterilely accommodate variable types and sizes of fluid reservoirs. In some embodiments, the plurality of fasteners comprises quick attachment type coupling. In some embodiments, the plurality of fasteners comprises at least one one-click type coupling. In some embodiments, various fasteners can be coupled to the support place at various desired locations. In some embodiments, at least one fastener comprises a bent needle. In some embodiments, one or more fasteners are configured to accommodate at least one fitting. In some embodiments, one or more fasteners and/or fittings comprise one or more apertures at various internal diameters to fit at least one barrel and/or finger flange of at least one fluid reservoir.

An aspect of some embodiments of the invention relates to a method of loading variable types and sizes of fluid reservoirs a self-injector. In some embodiments, the method comprises one or more fasteners sized and fitted for a barrel and finger flange of a selected fluid reservoir. In some embodiments, the method comprises optionally, selecting at least one fitting sized and fitted for a barrel and finger flange of a selected fluid reservoir. In some embodiments, the method further comprises optionally sliding or coupling one or more fittings onto the barrel or finger flange of the fluid reservoir. In some embodiments, the method further comprises sliding or coupling one or more fasteners onto the barrel or finger flange of the fluid reservoir. In some embodiments, the method further comprises inserting a tip of a fluid reservoir into an aperture in a needle portion of the injector. In some embodiments, the method further comprises optionally inserting a tip of a fluid reservoir into an aperture in a needle-bearing fastener. In some embodiments, the method further comprises coupling the fasteners to a support plate. In some embodiments, the method further comprises connecting the fluid reservoir to a injector fluid reservoir plunger driving system.

INTRODUCTION

Reference is now made to FIG. 1, which is a side view simplified illustration of a patch type self-injector as described in US Provisional Patent Application U.S. 62/284, 806 and is hereby incorporated in its entirety. Self-injector 100 comprises a bent needle 102, e.g., bent at a 90 degree angle coupled to a cartridge 104. Cartridge 104 may be pre-filled with an injectable. Cartridge 104 may be mounted on a support plate 106 and include a plunger 108 driven by electric motor driving gear 110. Following an injection procedure, cartridge 104 may be disposed of and replaced by a new pre-filled cartridge.

The injector powertrain and plunger driving systems are explained in detail in the above referenced US Provisional Patent Application U.S. 62/284,806 and will therefore not be repeated herein.

Optional Components of a Modular Self-Injector-Fluid Reservoir Coupling System.

Figure 2A:
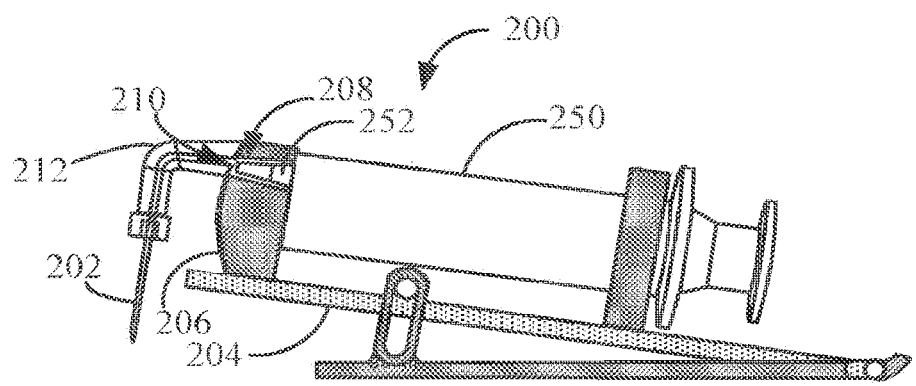
FIGS. 2A and 2B are side view simplified illustrations of optional exemplary embodiments of a modular patch type self-injector.
Figure 2B:
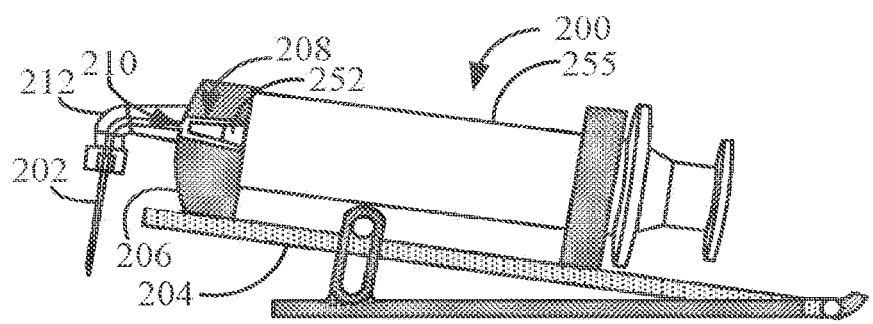

Reference is now made to FIGS. 2A, 2B and 2C, collectively referred to as FIG. 2, which are side view simplified illustrations of optional exemplary embodiments of a modular patch type self-injector. As shown in FIG. 2, a self-injector 200 may be sized and fitted to accommodate variable types and sizes of fluid reservoirs. As in the example of FIG. 1, in some embodiments, auto-injector 200 comprises a bent needle 202, e.g., bent at a 90 degree angle. As explained in greater detail elsewhere in the disclosure, in some embodiments, self-injector 200 comprises a support plate 204 and at least a needle 202-bearing portion 206. In some embodiments, needle-bearing portion 206 comprises at least a bore 208 sized and fitted to accommodate a fluid reservoir 250/255 tip 252. In some embodiments, bore 208 comprises an aperture 210 leading to the bent portion 212 of needle 202. In some embodiments, at least a portion of needle 202 sealingly extends through aperture 210 and into bore 208. In some embodiments, needle-bearing portion 206 is fixed on support plate 204.

In some embodiments, shown in FIG. 2A, bore 208 is disposed eccentrically within needle-bearing portion 206 to accommodate an eccentric tip fluid reservoir. In some embodiments, shown in FIG. 2B, bore 208 is disposed centrally within needle-bearing portion 206 to accommodate a regular (central) tip fluid reservoir.

Optional Examples of Injector-Fluid Reservoir Couplings

Figure 3A:
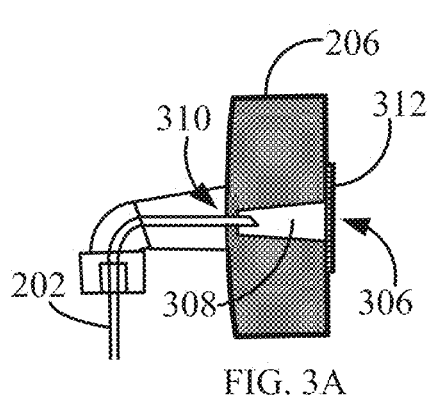
FIGS. 3A-3P are cross-section section and perspective view simplified illustrations of exemplary embodiments of injector-fluid reservoir couplings.

Commonly used fluid reservoir tips include slip or push on tips and Luer lock type tips. Plastic fluid reservoirs comprise plastic tips of both types whereas glass fluid reservoir tips are commonly made of metal. Some glass fluid reservoirs comprise glass slip-on type tips. The commonly used fluid reservoir-needle coupling practice attempts to maintain a sterile injectable passageway however this may be challenging at times. The common practice is to store both fluid reservoirs and needles each in a sterile pouch to limit their exposure time to the environment from the moment of removal from the pouch until the moment of injection. This practice is not practical when it comes to self-injectors and especially patch-type self-injectors.
Slip/Push-on Type Reference is now made to FIGS. 3A-3P, collectively referred to as FIG. 3, which are cross-section section and perspective view simplified illustrations of exemplary embodiments of injector-fluid reservoir couplings. The exemplary embodiments of FIGS. 3A-3L depict one or more adaptors that couple needle 202 to one or more various fluid reservoir tip types. For example, FIG. 3A, illustrates needle-bearing portion 206 comprising an adaptor 302 sized and fitted for coupling needle 202 to a slip or push-on type fluid reservoir tip 352. A centrally disposed bore 308 opens on one side to an opening 306 facing a fluid reservoir to receive a fluid reservoir tip and ends on the opposite side at an aperture 310 on the opposite side sized to sealingly accommodate at least a portion of needle 202. Optionally, in some embodiments, bore 308 comprises cone geometry. In some embodiments, bore 308 comprises cylinder geometry. Optionally and as also shown in FIG. 3C, in some embodiments, needle-bearing portion 206 may further comprise a resilient fitting 312 attached adhesively or by any other suitable method over opening 306. In some embodiments, fitting 312 may comprise an aperture 314 sized to accommodate a correspondingly sized slide-on type fluid reservoir tip. In some embodiments, when at least a portion of a fluid reservoir 350 is urged against the resilient fitting when locked into place in the injector, resilient fitting 312 stops possible leaks from the fluid reservoir tip-needle coupling.

Figure 3B:
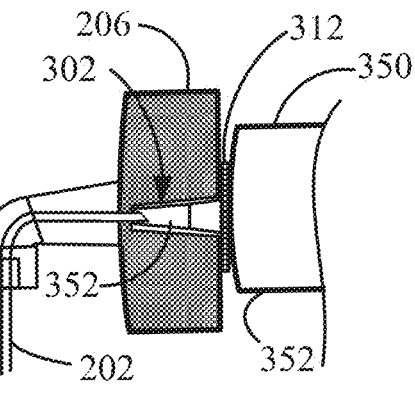
Figure 3C:
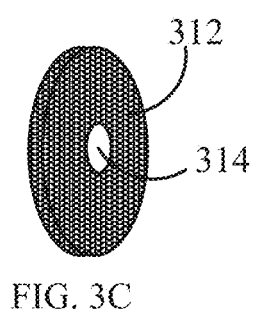

In some embodiments, fitting 312 may be made of a resilient type suitable material, e.g., Silicone to act as a seal and seal opening 306 when a fluid reservoir barrel 352 is urged against needle-bearing portion 206 as shown in FIG. 3B.

Figure 3D:
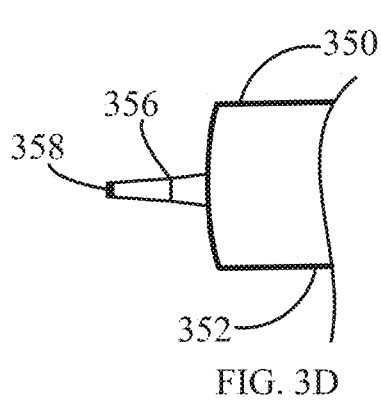
Figure 3E:
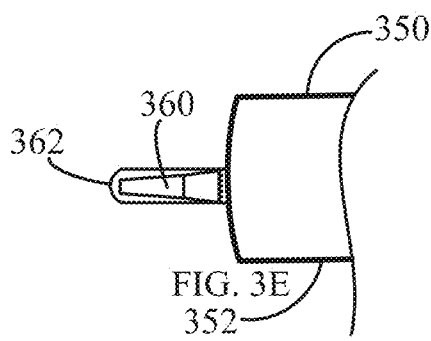
Figure 3F:
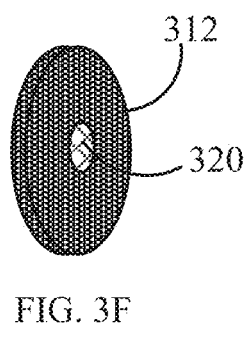

As illustrated in FIGS. 3A and 3B, in some embodiments, end of needle 316 may at least partially extend into bore 308 and into a lumen of a fluid reservoir tip 354 when a fluid reservoir 350 is coupled to the self-injector. As shown in FIGS. 3D and 3E, tips of a fluid reservoir 350 may be sealed for sterility. For example, an opening of a fluid reservoir tip 356 (FIG. 3D) may be sealed by a membrane 358, or, alternatively, a fluid reservoir tip 360 (FIG. 3E) may be covered by a protective sheath 362. In some embodiments, when coupled to a fluid reservoir 350, end 316 of needle 202 extending into bore 308 is configured to break most types of fluid reservoir tip seals protecting sterility of the injectable inside fluid reservoir 350. Ion some embodiments, and shown in FIG. 3F, fitting 312 aperture 314 may be sealed by a membranous seal 320. In some embodiments, when self-injector 200 is coupled to a fluid reservoir 350, a tip 356/360 of fluid reservoir 350 may break membranous seal 320.

Luer-Lock Type

Figure 3G:
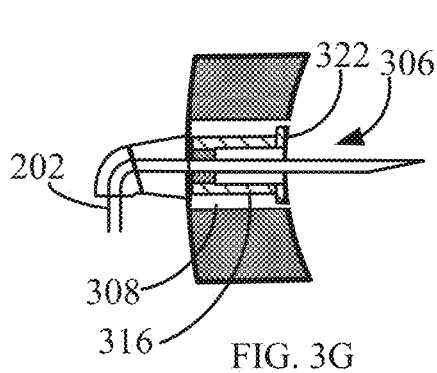
Figure 3H:
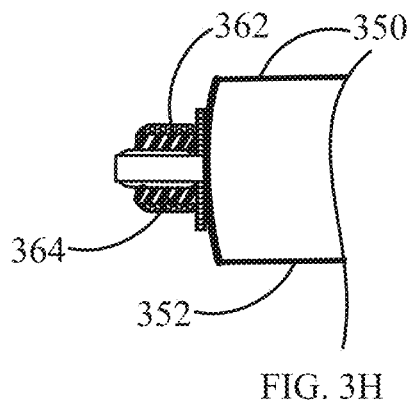
Figure 3I:
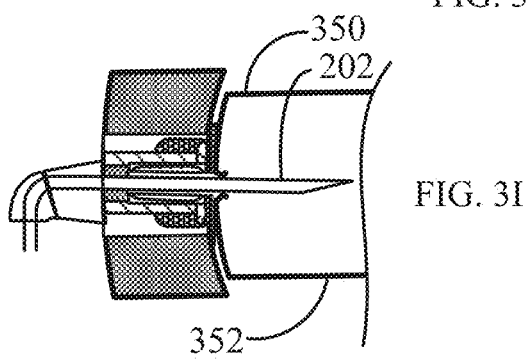

Referring now to FIGS. 3G-3I which illustrate self-injector 200 comprising bent needle 202 and Luer-lock coupling 316 sized and fitted to receive a fluid reservoir 350 with a male Luer-lock type tip 362. In some embodiments, Luer-lock coupling 316 comprises a cylinder sealingly coupled at one end to needle 202 and injector 200 and comprising a tabbed rim 322 on the opposite end that opens toward bore 308 opening 306. In some embodiments, tabbed rim 322 is configured to thread into a sleeve 364 on a male Leur-lock fluid reservoir tip 362. FIG. 3I shows Luer-lock coupling 316 and Luer-lock type fluid reservoir 350 tip 362 in a fully mated configuration.

Figure 3J:
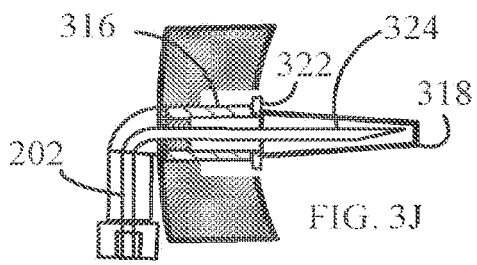
Figure 3L:
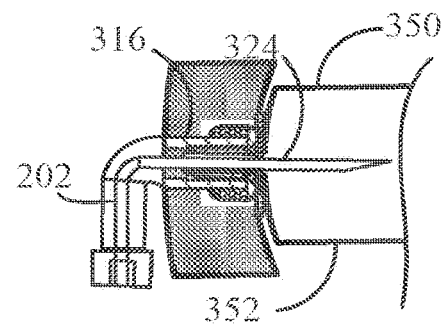
Figure 3K:
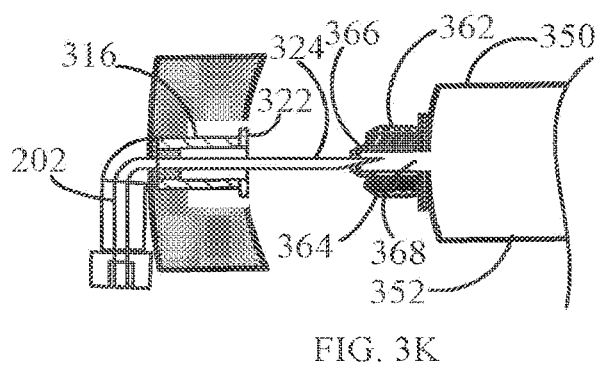

The exemplary embodiment depicted in FIGS. 3J-3L illustrates a Luer lock coupling system similar to that described elsewhere in the disclosure. Optionally, in some embodiments and as shown in FIG. 3J, end 324 of bent needle 202 extending beyond Luer-lock coupling 316 tabbed rim 322 comprises a protective sheath 318 configured to maintain sterility needle end 324. In some embodiments, protective sheath 318 is made of a pliable membranous material e.g., rubber, polyurethane or any other suitable material. In some embodiments, when mated as shown in FIG. 3K, a rim 366 of male Luer lock fluid reservoir 350 tip 362 urges protective sheath 318 against needle end 324. In some embodiments and as shown in FIG. 3K, needle end 324 breaks protective sheath 318 as it enters into the lumen 368 of fluid reservoir Luer lock tip 362. FIG. 3L shows Luer-lock coupling 316 and Luer-lock type fluid reservoir 350 tip 362 in a fully mated configuration. Additionally and optionally, in some embodiments, fluid reservoir male Luer lock tip 316 comprises a seal similar to seal 358 of fluid reservoir tip 356.

Figure 3N:
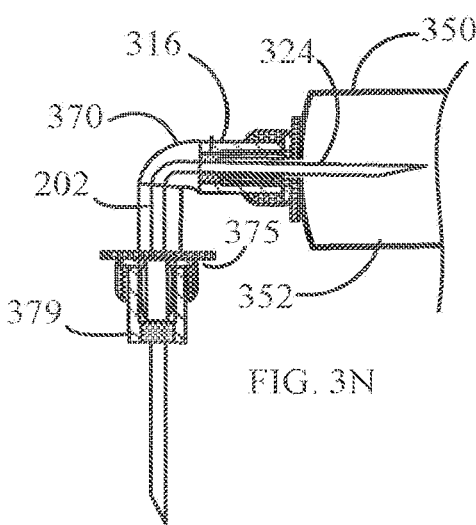
Figure 3M:
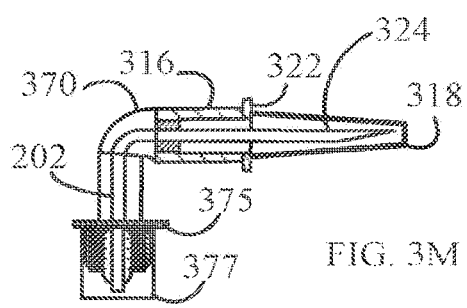

In some embodiments and as shown in FIGS. 3M and 3N, self-injector may be comprise a bent needle adaptor 370 comprising a fluid reservoir coupling similar to the examples described elsewhere in the disclosure and a second coupling 375 at a second end of the adaptor 370. In the example depicted ion FIGS. 3M and 3N second coupling 375 comprises a Leur lock tip. A cover 377 protects second coupling 375 from the environment and maintains the sterility of needle adaptor 370. In some embodiments, adapter 370 provides the freedom to couple a standard needle 379 to self-injector 200. In the exemplary embodiment shown in FIG. 3N, protective cap 377 has been removed and a Leur lock tip needle 379 is coupled to needle adaptor 370 and fluid reservoir 350.

Figures 3O, 3P:
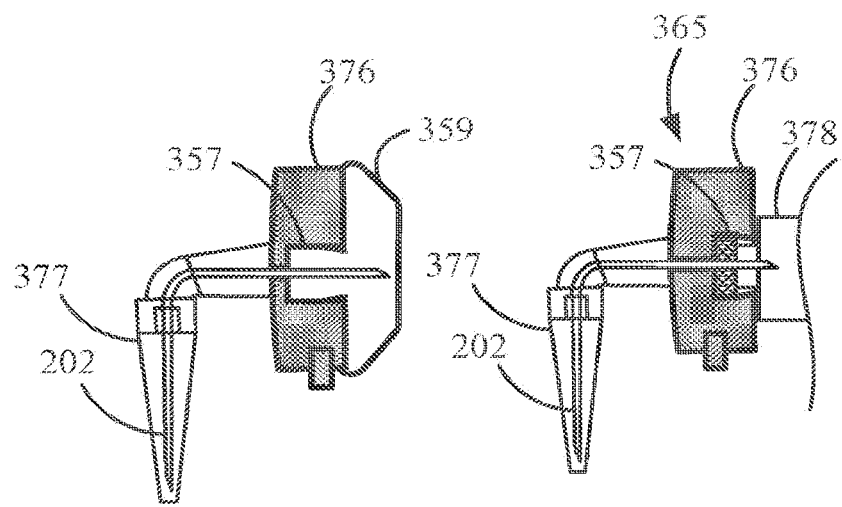

As shown in FIGS. 3O and 3P, an exemplary embodiment of bent needle adaptor 376 comprises a vial adaptor 357 such as, for example a Medimop Medical Projects Ltd. vial adaptor described in U.S. Pat. No. 7,326,194. In some embodiments, bent needle adaptor 376 comprises a sterile cover 359. In some embodiments, bent needle adaptor 376 comprises needle cap 377. Optionally and alternatively and as shown in FIG. 3P, bent needle adaptor 376 may be attached to an empty vial 378 to form a single non-sterile self-injector cartridge unit 365. In some embodiments, cartridge unit 365 can then be sterilized and filled with an injectable.

Optional Examples of Fasteners and Fittings

An aspect of some embodiments of the invention relates to a self-injector comprising a modular fluid reservoir-injector coupling system. Self-injectors and specifically patch self-injectors are designed to avoid movement of the injection needle in the tissue during the injection process and thus to minimize pain associated with the injection. This is achieved by various cou0pling methods that fixedly attach the injection needle and/or the fluid reservoir cartridge to the self-injector housing.

Reference is now made to FIGS. 4A-4H, collectively referred to as FIG. 4, which are plan and perspective view simplified illustration of exemplary embodiments of a modular fluid reservoir-injector coupling system. In the examples depicted in FIG. 4, self-injector 200 comprises one or more fasteners 402, sized and fitted to accommodate at least a barrel 452 or a finger flange 454 of a fluid reservoir 450. In some embodiments and as shown in FIGS. 4A and 4B, injector 200 comprises one or more fasteners configured to couple variable types and sizes of fluid reservoirs to self-injector 200. As shown in FIG. 4A, in some embodiments, a fastener 404 comprises ring geometry sized and fitted to slide onto a fluid reservoir barrel of a corresponding diameter. In some embodiments, fastener 404 further comprises at least one protrusion 406 extending from the periphery of fastener 404. In the exemplary embodiment depicted in FIG. 4A protrusion 406 extends tangentially from the ring of fastener 404, however protrusion 406 may extend radially or in any other suitable geometric configuration. In some embodiments, protrusion 406 is oriented parallel at least to a surface 408 of a support plate 410. In the exemplary embodiment illustrated in FIG. 4A, at least one protrusion 406 is fixedly coupled to the support plate 410 by at least one retention member. In the example shown in FIG. 4A, the attachment member comprises a retention cantilever 412. In some embodiments, retention lever 412 are elastic and/or comprise at least an elastic coupling to support plate 410. However, the attachment member may comprise any type of suitable attachment mechanism. In some embodiments, retention cantilever 412 is configured to releasably couple fastener 404 protrusion 406 to support plate. FIGS. 4B and 4C illustrate an exemplary embodiment in which fastener 414 comprises an inverted U geometry. In some embodiments, support plate 410 a plurality of notches 416 configured to accommodate legs 418 of fastener 414. In some embodiments, support plate 410 notches 416 comprise retention cantilevers 420 configured to releasably couple fastener 414 to support plate by fitting into one or more corresponding recesses 422 in legs 418. Optionally, a plurality of recesses 422 supports adjustment of the internal radius of fastener 414 by adjusting the depth of insertion of fastener 414 one or more legs 418 into support plate 410. Thus, a plurality of recesses 422 renders fastener 414 to be configured to size and fit a variety of fluid reservoir sizes.

As shown in FIG. 4D, in some embodiments, support plate 410 comprises a plurality of attachment points 412/416 distributed in a fashion that allows fasteners 402/414/424 to be coupled to support plate 410 at varying distances from needle portion 206 to accommodate fluid reservoirs of varying lengths. In some embodiments, attachment points 412/416 optionally comprise cantilevers 420 of the type shown in FIG. 4A. In some embodiments, attachment points 412/416 optionally comprise notches 416 and retention cantilevers 420 configured to releasably couple fasteners of the type depicted in FIGS. 4B and 4C. In some embodiments, attachment points 412/416 optionally comprise sliding hinges and retention levers in a configuration shown in FIGS. 4E and 4F. Additionally and optionally, attachment points 412/416 may comprise any similar suitable attachment mechanism other than the exemplary embodiments described herein.

FIGS. 4E and 4F illustrate an exemplary embodiment in which fastener 424 comprises a hinged inverted U geometry. In the example in FIGS. 4E and 4F one leg 426 comprises a sliding hinge 428 configured to form a large gap when open to release or receive a fluid reservoir barrel 452. In the closed configuration shown in FIG. 4E, fastener 424 non-hinged leg 426 is locked in place by a retention cantilever 420.

In some embodiments, at least one of fasteners 402/414/424 comprises the same size to fit onto the same support plate 410. In some embodiments and as shown in FIGS. 4G and 4H, fasteners 402/414/424 are fitted with one or more ring geometry fittings 430 (FIG. 4H) at various diameters sized and fitted to a corresponding diameter of a specific fluid reservoir barrel. In some embodiments, fittings 430 are configured to slide onto a barrel 452 of a fluid reservoir 450 and provide sufficient friction when a fastener, e.g. fasteners 414/424 is in the closed configuration to prevent axial slippage and movement of fluid reservoir barrel 452 in respect to support plate 410.

FIGS. 4G and 4H depict a fastener of the type illustrated in FIGS. 4B and 4C, however fittings 430 may be fitted in any one of the fasteners described herein or any other similar type of fastener.

Optional Examples of Adaptor-Fluid Reservoir Couplings and Fasteners Positioning In order to secure fixed coupling of a fluid reservoir to a self-injector, fasteners such as fasteners 420/414/424 need to be adjusted to a length of a fluid reservoir barrel in addition to fixing the fluid reservoir to a surface such as support plate 410. In most cases this can be achieved by sliding the fastener along the fluid reservoir barrel as described elsewhere in the disclosure and/or couple a fastener to a finger flange of the fluid reservoir. The structure of modular support plate 410 described elsewhere in the disclosure allows for positioning a fastener at almost any desired location when fitted to a fluid reservoir barrel or finger flange. Reference is now made to FIGS. 5A-5G, which are part sectional side view simplified illustrations of positioning of fasteners coupling a fluid reservoir to a self-injector.

Figure 5A:
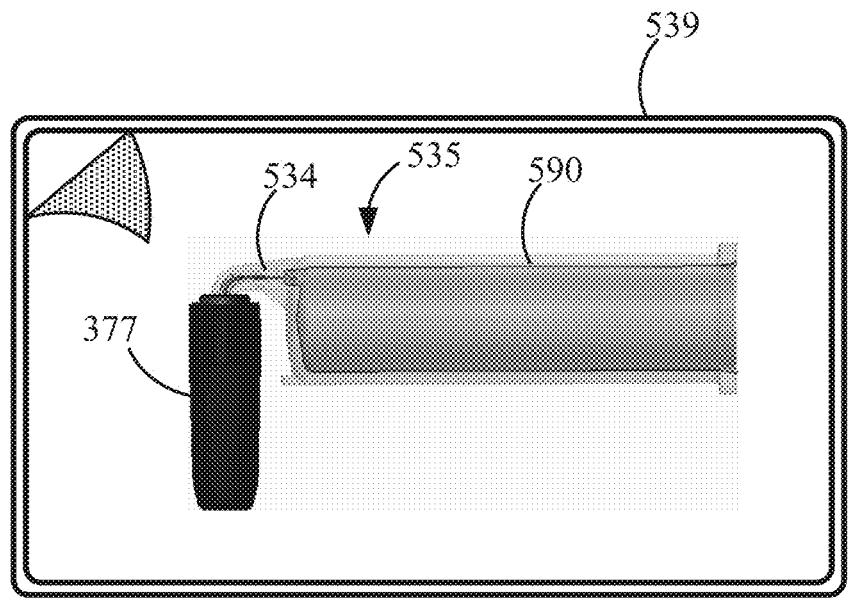
FIGS. 5A, 5B, 5C, 5D, 5E, 5F and 5G are part sectional side view simplified illustrations of positioning of fasteners coupling a fluid reservoir to a self-injector.
Figure 5B:
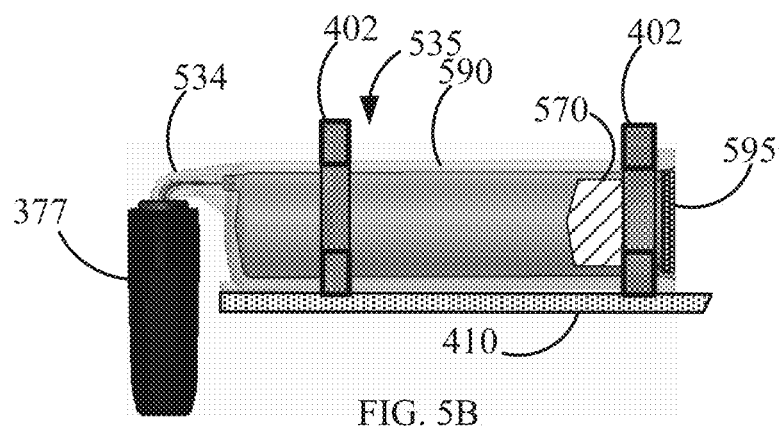
Figure 5C:
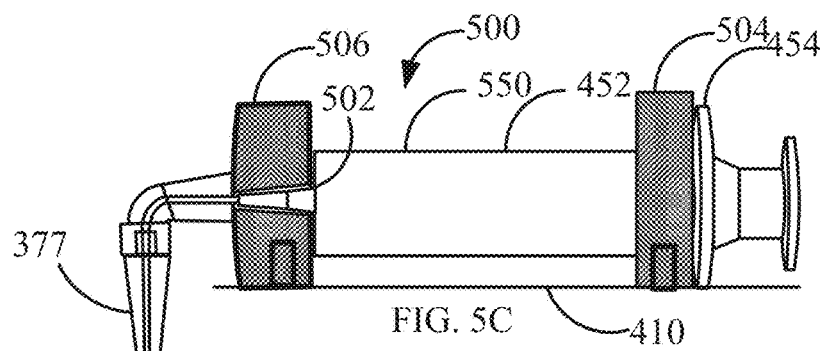

In the exemplary embodiment depicted in FIG. 5A an empty fluid reservoir 590 is coupled to a needle-bearing portion 534 to form a single integral self-injector cartridge unit 535. In some embodiments, cartridge unit 535 is sterile. In some embodiments, cartridge unit 535 is non-sterile. In some embodiments, cartridge unit 535 is sterilized, filled with an injectable in a sterile fashion and provided sterile, sealed and ready for use. As shown in the exemplary embodiments illustrated in FIG. 5B, a sterilely pre-filled cartridge unit 535 is coupled to support plate 410 by one or more fasteners 402 (FIG. 4A). In some embodiments, cartridge unit 535 comprises a plunger 570 and is sealed after filling for sterility with a seal 595. In some embodiments, cartridge unit 535 is delivered unsterile for sterilization and filling in an envelope e.g., a plastic blister 539. As shown in FIG. 5C, a fluid reservoir 550 e.g., 20 cc fluid reservoir, comprising a slip-on tip is mounted onto self-injector 500. In the exemplary embodiment shown in FIG. 5C tip 502 is shown to be inserted into a needle-bearing portion 506 in a fashion described elsewhere in the disclosure and will not be repeated. In the exemplary embodiment depicted in FIG. 5C, needle-bearing portion 506 comprises a coupling similar to that of fastener 504 and is reversibly coupled to support plate 410. In some embodiments, one or more fasteners 504 of a form and function of which is described elsewhere in the disclosure and will not be repeated are positioned along barrel 452 at least one of which abutting a finger flange 454 coupling a barrel 452 of fluid reservoir 450 to support plate 410. In some embodiments, when closed, fastener 504 provides sufficient friction against barrel 452 to prevent axial slippage and movement of barrel 452 in respect to support plate 410. Alternatively and optionally, in some embodiments, a fitting of a type described elsewhere in the disclosure may be fitted inside fastener 504 and provide sufficient friction against barrel 452 to prevent axial slippage and movement of barrel 452 in respect to support plate 410.

Figures 5D, 5E:
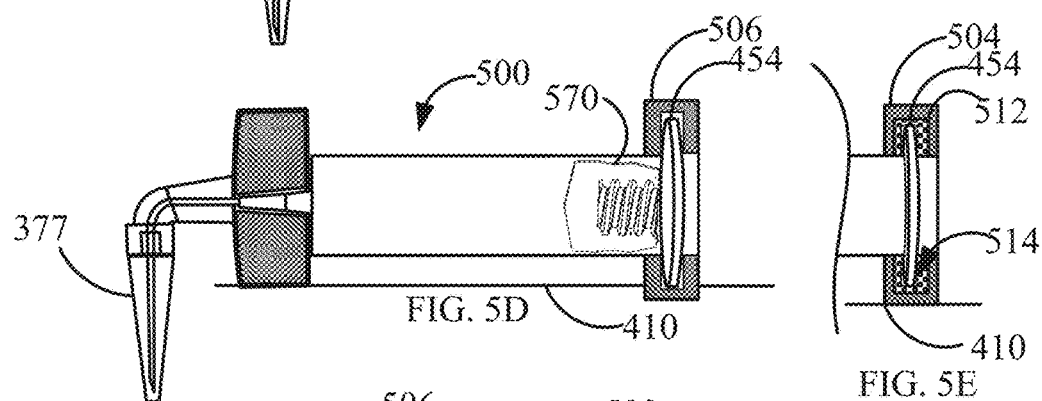

Alternatively and optionally and as shown in FIG. 5D, in some embodiments, a fastener 506 comprises a radial slot 508 along an internal wall 510 sized and fitted to accommodate a corresponding sized fluid reservoir finger flange 454. Alternatively and optionally and as shown in FIG. 5E, in some embodiments, a fastener of the type of fastener 504 comprises a fitting 512 fitted inside fastener 504 comprising a radial slot 514 along an internal wall of fitting 512 is sized and fitted to accommodate a corresponding sized fluid reservoir finger flange 454. In some embodiments, fitting 512 provides sufficient friction against finger flange 454 to prevent axial slippage and movement of barrel 452 in respect to support plate 410. In FIG. 5D a fluid reservoir plunger has been replaced with a plunger 570 configured to be driven by a self-injector 500 plunger driving system (not shown).

Figure 5F:
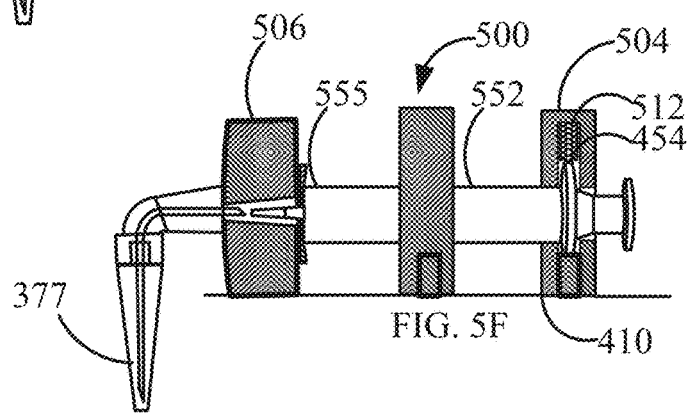

Alternatively and optionally, modular fluid reservoir-injector coupling system is shown in FIG. 5F coupling a small sized fluid reservoir 555 e.g., 5 cc fluid reservoir to self-injector 500. fluid reservoir 555 slip-on tip is shown to be inserted into a needle-bearing portion 506 in a fashion described elsewhere in the disclosure and will not be repeated. In some embodiments, one or more fasteners 504 of a form and function of which is described elsewhere in the disclosure and will not be repeated are positioned along barrel 552 at least one of which abutting a finger flange 554 coupling a barrel 552 of fluid reservoir 555 to support plate 410. In some embodiments, when closed, fastener 504 provides sufficient friction against barrel 552 to prevent axial slippage and movement of barrel 552 in respect to support plate 410. Alternatively and optionally, in some embodiments, a fitting 430 of a type described elsewhere in the disclosure may be fitted inside fastener 504 and provide sufficient friction against barrel 552 to prevent axial slippage and movement of barrel 552 in respect to support plate 410.

Figure 5G:
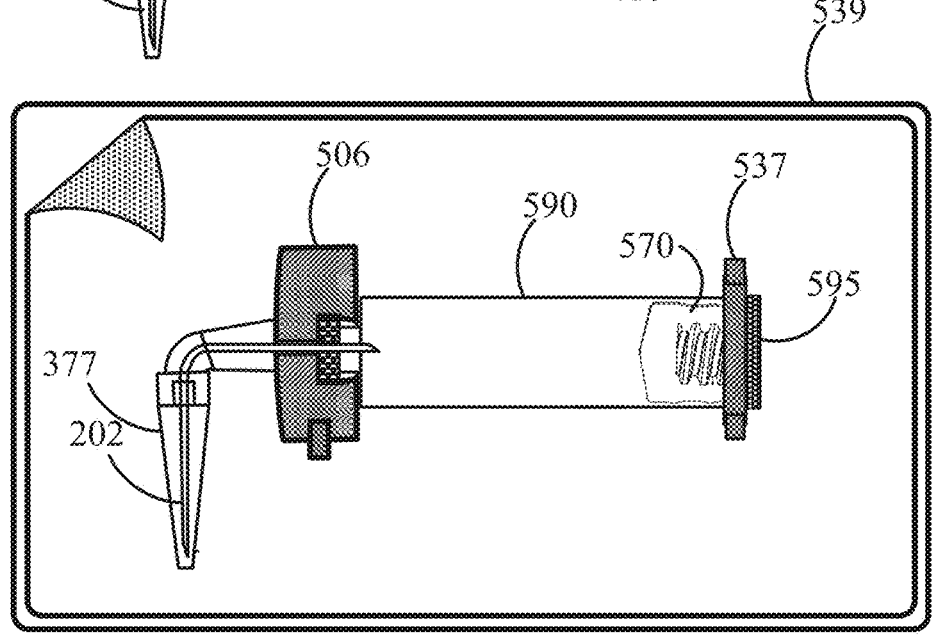
Figure 6:
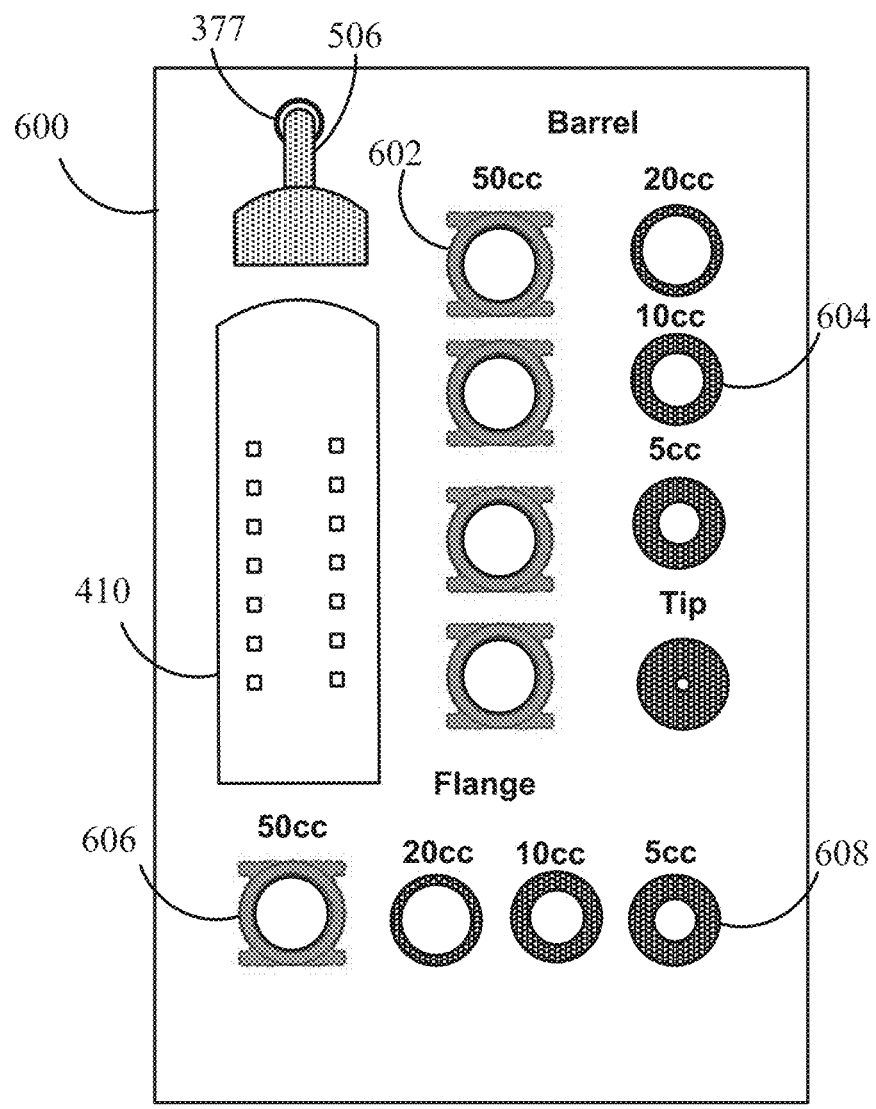
FIG. 6 is a plan view simplified illustration of a home kit for self-injection.

In the embodiment shown in FIG. 5F, a fitting 512 fitted inside fastener 504 is sized and fitted to accommodate corresponding sized fluid reservoir finger flange 554. As shown in FIG. 5G, needle-bearing portion 506 comprises a coupling 537 to support plate similar to that of fasteners 504 or any type of fastener coupling described elsewhere in the disclosure and is reversibly coupled to support plate 410. As shown in FIG. 5G, in some embodiments, a finger-flangeless fluid reservoir 590 is sealingly attached to needle-bearing portion 506. In the exemplary embodiment depicted in FIG. 5G, fluid reservoir 590 is a pre-filled vial attached to needle-bearing portion 506 and fitted with a fastener 402 (FIG. 4C) to be mounted onto support plate 410 as explained elsewhere in the disclosure. In some embodiments, needle-bearing portion 506 comprises a needle 202 protective cap 377. In some embodiments, fluid reservoir 590 is sealed for sterility with a seal 595. In some embodiments, pre-filled fluid reservoir 590 attached to needle-bearing portion 506 is delivered in an envelope e.g., a plastic blister 539. Reference is now made to FIG. 6, which is a plan view simplified illustration of a home kit for self-injection. As shown in FIG. 6, in some embodiments a kit 600 comprises a self-injector, represented in FIG. 6 by a modular support plate 410, a plurality of fasteners 602 and a variety of fittings 604 comprising various internal diameters.

Additionally and optionally, in some embodiments kit 600 may comprise markings that assist a user to select the correct fastener or fitting for the corresponding selected fluid reservoir. For example, in the exemplary embodiment depicted in FIG. 6, for a selected 50 cc fluid reservoir the user may select only fasteners to sufficiently couple the fluid reservoir to the self-injector. For a smaller sized fluid reservoir, e.g., 10 cc fluid reservoir the user may select a fastener and a fitting marked "10 cc" to be inserted into the fastener. In some embodiments, kit 600 comprises clearly marked indicators as to fitting sizes and types of fasteners and fittings e.g., "5 cc", "10 cc", "20 cc", "50 cc", "tip", "Flange", etc.

In some embodiments, a user would use kit 600 to couple a fluid reservoir to a self-injector by removing the self-injector from the kit and opening a cover to expose support plate 410. In some embodiments, the method further comprises coupling needle bearing portion 506 to the fluid reservoir. In some embodiments, needle bearing portion 506 comprises a needle protective cap 377. In some embodiments, the method further comprises selecting one or more fasteners 602 and sliding one or more fasteners on a barrel 452/552 of a fluid reservoir. Alternatively and optionally the method comprises coupling one or more fasteners 602 to support plate 410. Optionally, the method comprises inserting one or more fittings 604 into one or more fasteners 602 before sliding onto a barrel 452/552 of a fluid reservoir. Additionally and optionally, the method comprises selecting a finger flange fastener 606 and coupling the fluid reservoir flange to support plate 410. Optionally, the method comprises inserting one or more finger flange fittings 608 into one or more fasteners 602 before coupling the fluid reservoir flange to support plate 410. Optionally, the method comprises selecting at least one attachment points 412/416 and attaching a fastener 604/606 to the selected attachment points 412/416.

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An assembly comprising:
   an injector comprising:
      a base having an adhesive configured to adhere the injector to a skin surface, and
      a fluid reservoir; and
   an add-on comprising:
      an adaptor comprising at least one Luer lock coupling sized and shaped to couple said adaptor to the fluid reservoir, and
      a rigid and bent fluid path having a first end configured to penetrate tissue and a second end coupled to said adaptor,
   wherein when said add-on is coupled to said fluid reservoir, sterile fluid communication is secured between said fluid reservoir and said first end of said bent fluid path.

2. The assembly of claim 1, wherein said bent fluid path comprises a coupling at said second end sized and shaped to couple said bent fluid path to said adaptor and secure sterile fluid communication in-between.

3. The assembly of claim 1, further comprising at least one fastener sized and fitted to couple said fluid reservoir to the injector.

4. The assembly of claim 1, wherein said bent fluid path comprises a hollow needle.

5. The assembly of claim 4, wherein an end of the hollow needle extends beyond the adaptor.

6. The assembly of claim 1, wherein said bent fluid path is bent at a 90 degree angle.

7. The assembly of claim 1, wherein said fluid reservoir is a prefilled cartridge.

8. The assembly of claim 1, wherein said fluid reservoir is a syringe.

9. The assembly of claim 1, wherein said fluid reservoir is a vial.

10. The assembly of claim 1, wherein at least a portion of said fluid reservoir is made of glass.

11. The assembly of claim 1, wherein at least a portion of said fluid reservoir is made of a plastic material.

12. The assembly of claim 1, wherein said add-on is sterilizable en bloc.

13. The assembly of claim 1, wherein said adaptor is a vial adaptor.

14. The assembly of claim 1, further comprising a coupling sized and shaped to couple said add-on to the injector.

15. The assembly of claim 1, further comprising a cover configured to cover the first end of the bent fluid path.

16. The assembly of claim 1, further comprising a protective sheath configured to cover the second end of the bent fluid path.

17. The assembly of claim 1, wherein the injector comprising a plate configured to support the fluid reservoir, wherein the plate is movable relative to the base.

* * * * *